United States Patent
Richmond et al.

(10) Patent No.: US 10,588,699 B2
(45) Date of Patent: Mar. 17, 2020

(54) INTELLIGENT POSITIONING SYSTEM AND METHODS THEREFORE

(71) Applicants: Joshua Lee Richmond, Toronto (CA); Brent Andrew Bailey, Toronto (CA); Stephen B. E. McFadyen, Toronto (CA); Michael Wood, Toronto (CA); Abhijit Saxena, Toronto (CA); Kai Michael Hynna, Toronto (CA); Yanhui Bai, Toronto (CA)

(72) Inventors: Joshua Lee Richmond, Toronto (CA); Brent Andrew Bailey, Toronto (CA); Stephen B. E. McFadyen, Toronto (CA); Michael Wood, Toronto (CA); Abhijit Saxena, Toronto (CA); Kai Michael Hynna, Toronto (CA); Yanhui Bai, Toronto (CA)

(73) Assignee: SYNAPTIVE MEDICAL (BARBADOS) INC., Bridgetown (BB)

(*) Notice: Subject to any disclaimer, the term of this patent is extended or adjusted under 35 U.S.C. 154(b) by 237 days.

(21) Appl. No.: 15/725,355

(22) Filed: Oct. 5, 2017

(65) Prior Publication Data
US 2018/0055578 A1 Mar. 1, 2018

Related U.S. Application Data

(63) Continuation of application No. 15/116,249, filed as application No. PCT/CA2014/050875 on Sep. 15, 2014, now Pat. No. 9,827,054.

(30) Foreign Application Priority Data

Mar. 14, 2014 (WO) ................ PCT/CA2014/050271

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/064* (2013.01); *A61B 34/25* (2016.02); *A61B 34/37* (2016.02);
(Continued)

(58) Field of Classification Search
None
See application file for complete search history.

(56) References Cited

U.S. PATENT DOCUMENTS 5,820,545 A * 10/1998 Arbter ................ A61B 1/00147
600/117
6,468,265 B1 * 10/2002 Evans .................... A61B 34/32
600/103
(Continued)

*Primary Examiner* — Ryan Rink
(74) *Attorney, Agent, or Firm* — Ridout & Maybee LLP

(57) ABSTRACT

A medical navigation system is provided, comprising a computing device having a processor coupled to a memory, a tracking camera for tracking medical devices, and a display for displaying an image; an automated arm assembly electrically coupled to the computing device and controlled by a signal provided by the computing device, the automated arm assembly including a multi-joint arm having a distal end connectable to an effector that supports a surgical camera electrically coupled to the computing device; and a medical device having a tracking marker attachable to the medical device. The computing device is configured to position the automated arm assembly, based on an input command, in response to a position in space of the medical device such that a surgical site of interest remains within a field of view of the surgical camera, the position in space of the medical device determined by the computing device based on a signal provided to the computing device by the tracking camera; and display on the display an image provided by an image signal generated by the surgical camera.

18 Claims, 32 Drawing Sheets

(51) Int. Cl.
*G16H 40/63* (2018.01)
*G06F 19/00* (2018.01)
*A61B 34/00* (2016.01)
*A61B 34/37* (2016.01)
*A61B 90/00* (2016.01)
*A61B 17/00* (2006.01)
*A61B 90/25* (2016.01)

(52) U.S. Cl.
CPC ........ *A61B 90/361* (2016.02); *G06F 19/3481* (2013.01); *G16H 40/63* (2018.01); *A61B 90/25* (2016.02); *A61B 2017/00973* (2013.01); *A61B 2034/2055* (2016.02); *A61B 2034/2057* (2016.02); *A61B 2034/2059* (2016.02); *A61B 2034/2065* (2016.02); *A61B 2090/3612* (2016.02); *A61B 2090/3735* (2016.02); *A61B 2090/3983* (2016.02); *G06F 19/321* (2013.01)

(56) References Cited

U.S. PATENT DOCUMENTS

| | | | |
|---|---|---|---|
| 6,633,328 B1* | 10/2003 | Byrd | H04N 7/183 348/143 |
| 2002/0147384 A1* | 10/2002 | Uchikubo | A61B 1/0005 600/109 |
| 2003/0055410 A1* | 3/2003 | Evans | A61B 34/32 606/1 |
| 2009/0326556 A1* | 12/2009 | Diolaiti | A61B 1/00009 606/130 |
| 2014/0051921 A1* | 2/2014 | Miller | A61B 1/00009 600/103 |
| 2014/0314538 A1* | 10/2014 | Carter | A61B 90/50 414/744.3 |
| 2015/0109458 A1* | 4/2015 | Lee | G06T 7/80 348/175 |
| 2017/0172675 A1* | 6/2017 | Jarc | A61B 90/361 |

* cited by examiner

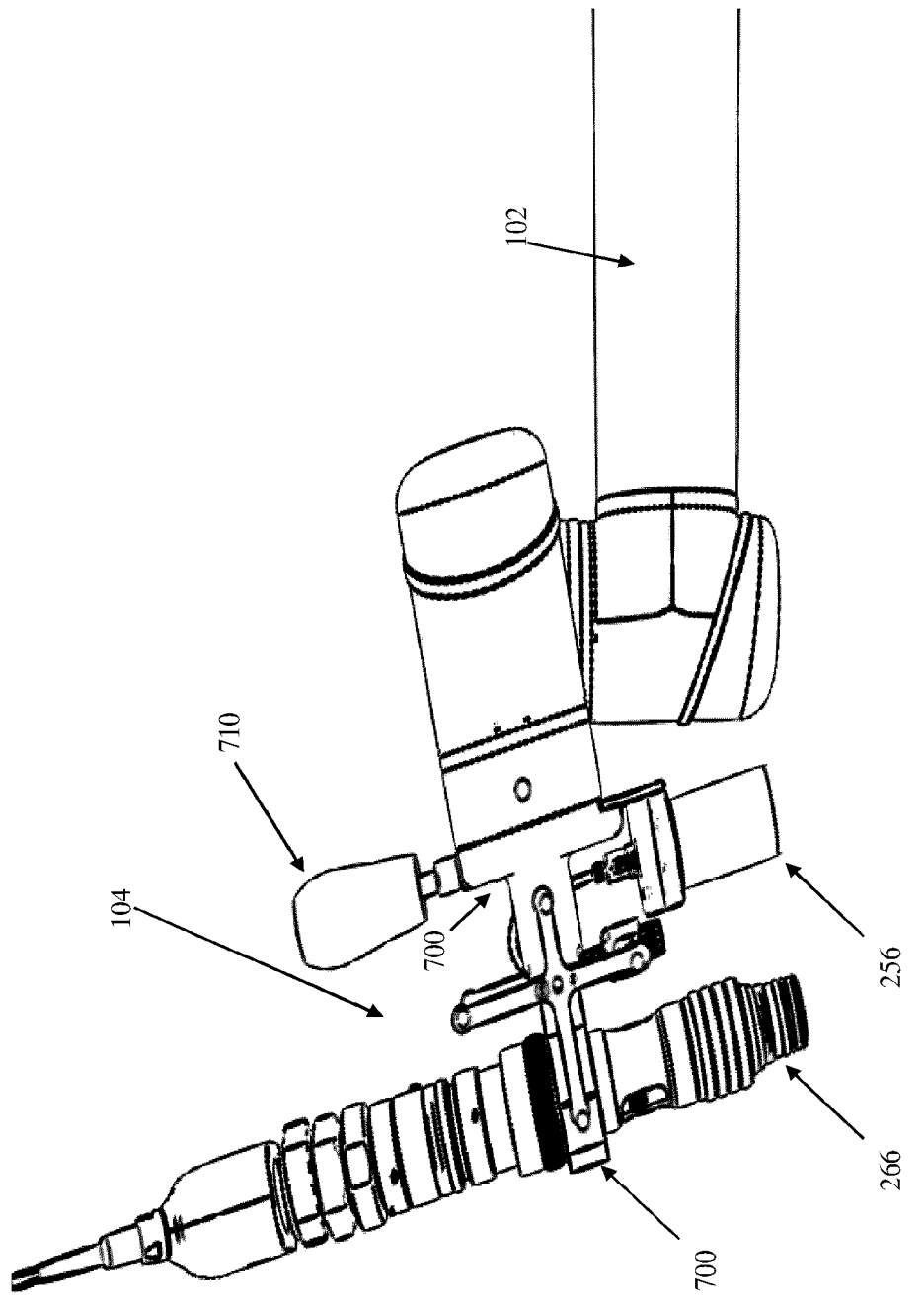

End Effector

End Effector

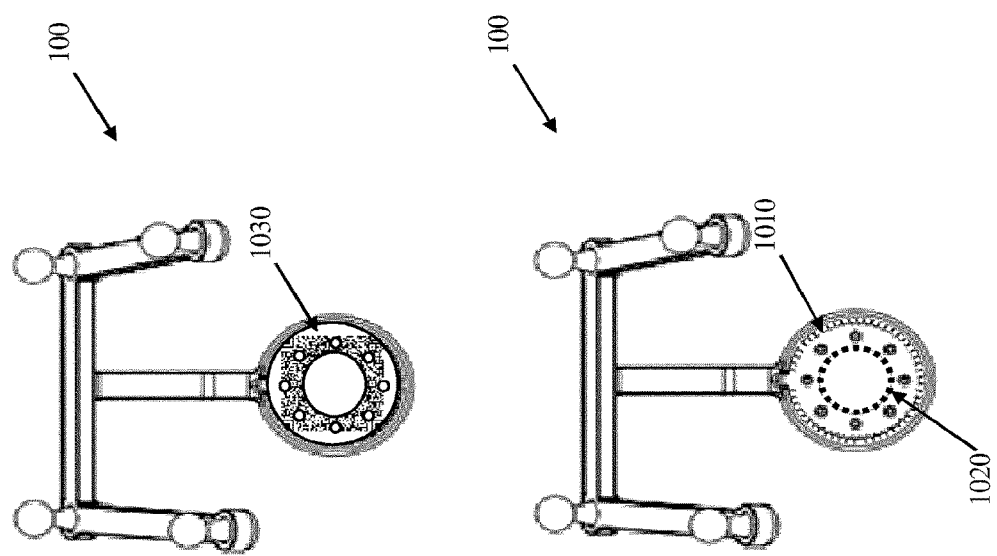

INTELLIGENT POSITIONING SYSTEM AND METHODS THEREFORE

This application is a continuation of U.S. patent application Ser. No. 15/116,249 filed Sep. 15, 2014 and claims priority to PCT Application No. CA2014050271, titled "INTELLIGENT POSITIONING SYSTEM AND METHODS THEREFORE" and filed on Mar. 14, 2014, the entire contents of which is incorporated herein by reference.

FIELD

The present disclosure relates to mechanically assisted positioning of medical devices during medical procedures.

BACKGROUND

Intracranial surgical procedures present new treatment opportunities with the potential for significant improvements in patient outcomes. In the case of port-based surgical procedures, many existing optical imaging devices and modalities are incompatible due a number of reasons, including, for example, poor imaging sensor field of view, magnification, and resolution, poor alignment of the imaging device with the access port view, a lack of tracking of the access port, problems associated with glare, the presences of excessive fluids (e.g. blood or cranial spinal fluid) and/or occlusion of view by fluids. Furthermore, attempts to use currently available imaging sensors for port-based imaging would result in poor image stabilization. For example, a camera manually aligned to image the access port would be susceptible to misalignment by being regularly knocked, agitated, or otherwise inadvertently moved by personnel, as well as have an inherent settling time associated with vibrations. Optical port-based imaging is further complicated by the need to switch to different fields of view for different stages of the procedure. Additional complexities associated with access port-based optical imaging include the inability to infer dimensions and orientations directly from the video feed.

In the case of port-based procedures, several problems generally preclude or impair the ability to perform port-based navigation in an intraoperative setting. For example, the position of the access port axis relative to a typical tracking device employed by a typical navigation system is a free and uncontrolled parameter that prohibits the determination of access port orientation. Furthermore, the limited access available due to the required equipment for the procedure causes methods of indirect access port tracking to be impractical and unfeasible. Also, the requirement for manipulation of the access port intraoperatively to access many areas within the brain during a procedure makes tracking the spatial position and pose of the access port a difficult and challenging problem that has not yet been addressed prior to the present disclosure. Thus, there is a need to consider the use of an intelligent positioning system to assist in access port-based intracranial medical procedures and surgical navigation.

SUMMARY

One aspect of the present description provides a medical navigation system comprising a computing device having a processor coupled to a memory, a tracking camera for tracking medical devices, and a display for displaying an image; an automated arm assembly electrically coupled to the computing device and controlled by a signal provided by the computing device, the automated arm assembly including a multi-joint arm having a distal end connectable to an effector that supports a surgical camera electrically coupled to the computing device; and a medical device having a tracking marker attachable to the medical device. The computing device is configured to position the automated arm assembly, based on an input command, in response to a position in space of the medical device such that a surgical site of interest remains within a field of view of the surgical camera, the position in space of the medical device determined by the computing device based on a signal provided to the computing device by the tracking camera; and display on the display an image provided by an image signal generated by the surgical camera.

The input command may be provided by at least one of a foot pedal, a joystick, a microphone receiving a voice instruction, a transducer detecting a gesture, and a wireless electronic device. The medical device may include at least one of a pointer and an access port, the surgical site of interest being a pointing end of the pointer and an axial view down a longitudinal axis of the access port, respectively.

Another aspect of the present disclosure provides a method for use in a medical navigation system having a computing device including a processor coupled to a memory, a tracking camera for tracking medical devices, and a display for displaying an image; and an automated arm assembly electrically coupled to the computing device and controlled by a signal provided by the computing device. The automated arm assembly includes a multi-joint arm having a distal end connectable to an effector that supports a surgical camera electrically coupled to the computing device. The method comprises positioning the automated arm assembly, based on an input command, in response to a position in space of a medical device such that a surgical site of interest remains within a field of view of the surgical camera, the position in space of the medical device determined by the computing device based on a signal provided to the computing device by the tracking camera; and displaying on the display an image provided by an image signal generated by the surgical camera.

Another aspect of the present disclosure provides a control system for tracking a medical device having a tracking marker attachable to the medical device. The control system comprises a computing device having a processor coupled to a memory, the computing device receiving a signal from a tracking camera for tracking medical devices; and an automated arm assembly electrically coupled to the computing device and controlled by a signal provided by the computing device, the automated arm assembly including a multi-joint arm having a distal end connectable to an effector that supports a surgical camera. The computing device is configured to position the automated arm assembly, based on an input command, in response to a position in space of the medical device such that a surgical site of interest remains within a field of view of the surgical camera, the position in space of the medical device determined by the computing device based on a signal provided to the computing device by the tracking camera; and display on the display an image provided by an image signal generated by the surgical camera.

Another aspect of the present disclosure provides a method for use in a control system having a computing device including a processor coupled to a memory, a tracking camera providing a signal to the computing device for tracking medical devices; and an automated arm assembly electrically coupled to the computing device and controlled by a signal provided by the computing device. The automated arm assembly includes a multi-joint arm having a distal end connectable to an effector that supports a surgical camera. The method comprises positioning the automated arm assembly, based on an input command, in response to a position in space of a medical device such that a surgical site of interest remains within a field of view of the surgical camera, the position in space of the medical device determined by the computing device based on a signal provided to the computing device by the tracking camera; and displaying on a display an image provided by an image signal generated by the surgical camera.

BRIEF DESCRIPTION OF THE DRAWINGS

Embodiments will now be described, by way of example only, with reference to the drawings, in which:

FIGS. 4A-E are exemplary embodiment of various components in an intelligent positioning system;

FIG. 10A-B is an illustration depicting tool characteristics that can be utilized in optical detection methods;

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

As used herein the term "Navigation system", refers to a surgical operating platform which may include within it an Intelligent Positioning System as described within this document.

As used herein the term "Imaging sensor", refers to an imaging system which may or may not include within it an Illumination source for acquiring the images.

As used herein, the term "tracking system", refers to a registration apparatus including an operating platform which may be included as part of or independent of the intelligent positioning system.

Several embodiments of the present disclosure seek to address the aforementioned inadequacies of existing devices and methods to support access port-based surgical procedures.

Figure 16A:
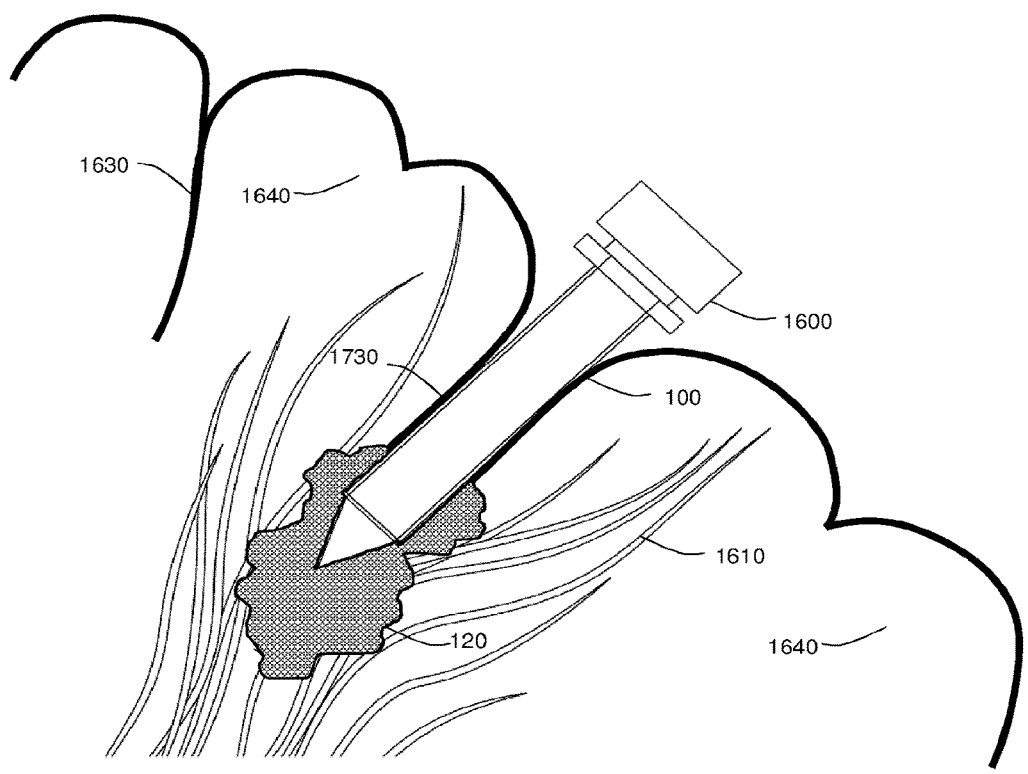
FIG. 16A-D are exemplary embodiments illustrating a port with introducer during cannulation into the brain.
Figure 16B:
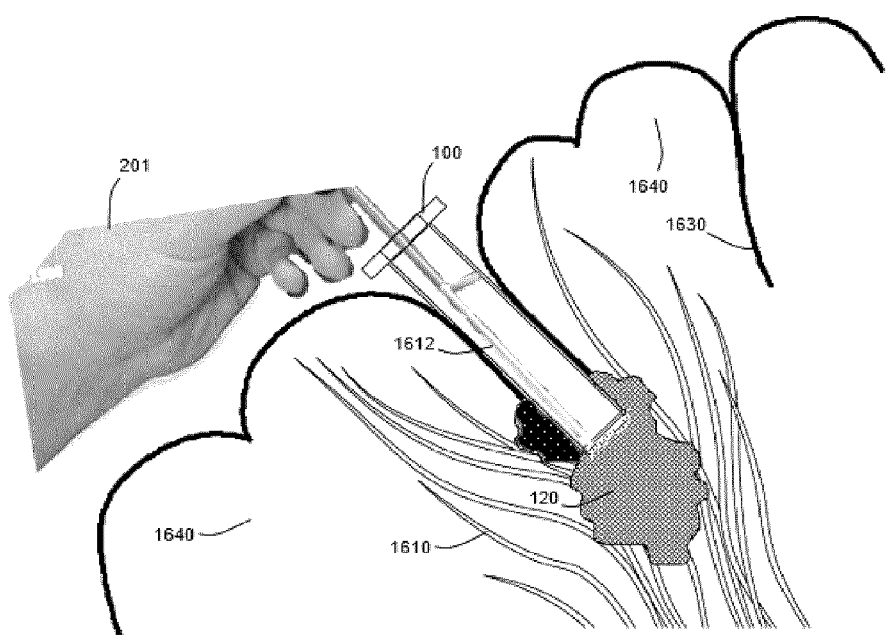

Minimally invasive brain surgery using access ports is a recently conceived method of performing surgery on brain tumors previously considered inoperable. One object of the present invention is to provide a system and method to assist in minimally invasive port-based brain surgery. To address intracranial surgical concerns, specific products such as the NICO BrainPath™ port have been developed for port-based surgery. As seen in FIG. 16A, port 100 comprises of a cylindrical assembly formed of an outer sheath. Port 100 may accommodate introducer 1600 which is an internal cylinder that slidably engages the internal surface of port 100. Introducer 1600 may have a distal end in the form of a conical atraumatic tip to allow for insertion into the sulci folds 1630 of the brain. Port 100 has a sufficient diameter to enable manual manipulation of traditional surgical instruments such as suctioning devices, scissors, scalpels, and cutting devices as examples. FIG. 16B shows an exemplary embodiment where surgical instrument 1612 is inserted down port 100.

Figure 1:
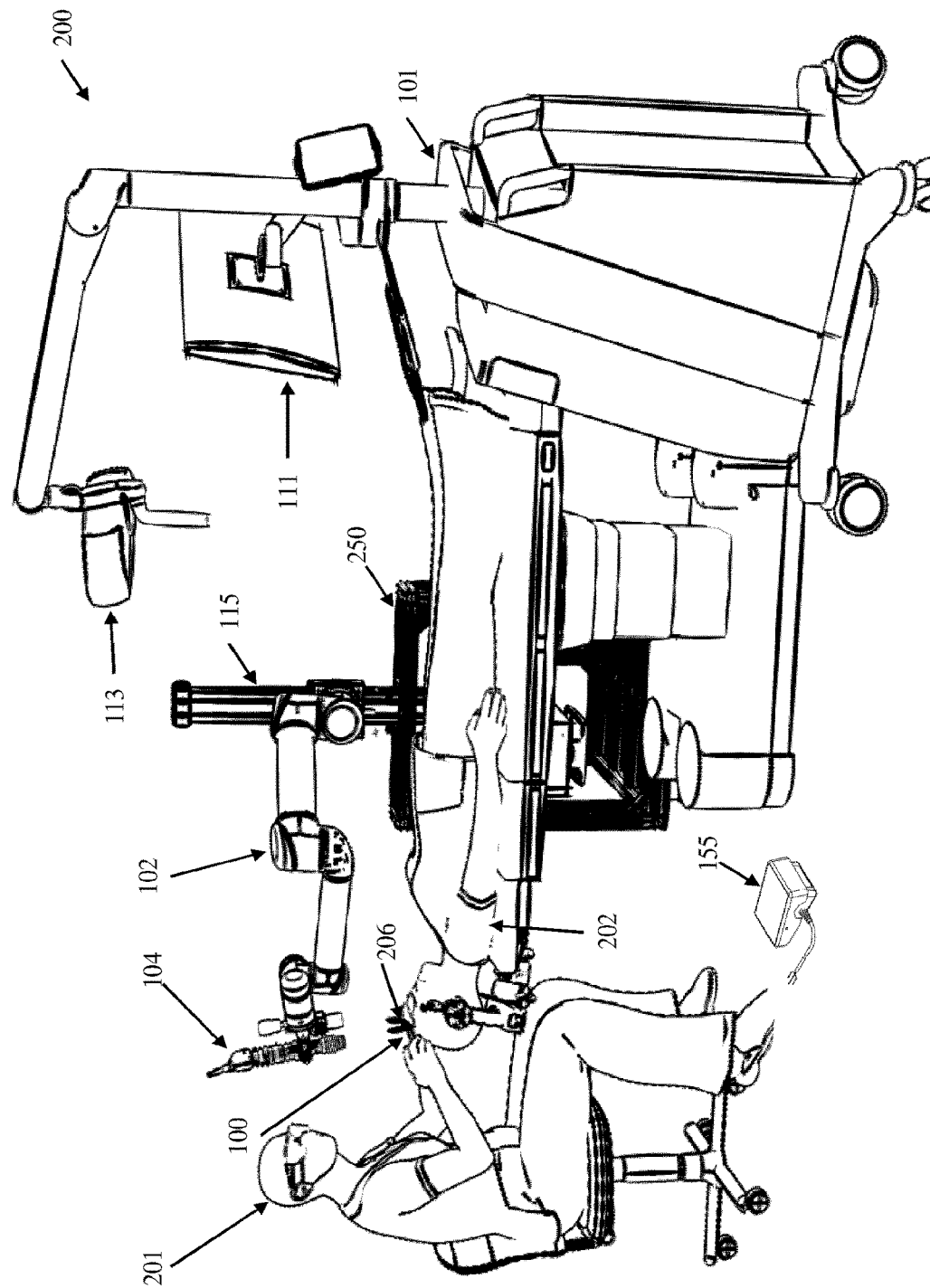
FIG. 1 is an exemplary embodiment illustrating system components of an exemplary surgical system used in port based surgery.

FIG. 1 is a diagram illustrating components of an exemplary surgical system used in port based surgery. FIG. 1 illustrates a navigation system 200 having an equipment tower 101, tracking system 113, display 111, an intelligent positioning system 250 and tracking markers 206 used to tracked instruments or an access port 100. Tracking system 113 may also be considered an optical tracking device or tracking camera.

In FIG. 1, a surgeon 201 is performing a tumor resection through a port 100, using an imaging device 104 to view down the port at a sufficient magnification to enable enhanced visibility of the instruments and tissue. The imaging device 104 may be an external scope, videoscope, wide field camera, or an alternate image capturing device. The imaging sensor view is depicted on the visual display 111 which surgeon 201 uses for navigating the port's distal end through the anatomical region of interest.

Figure 5A:
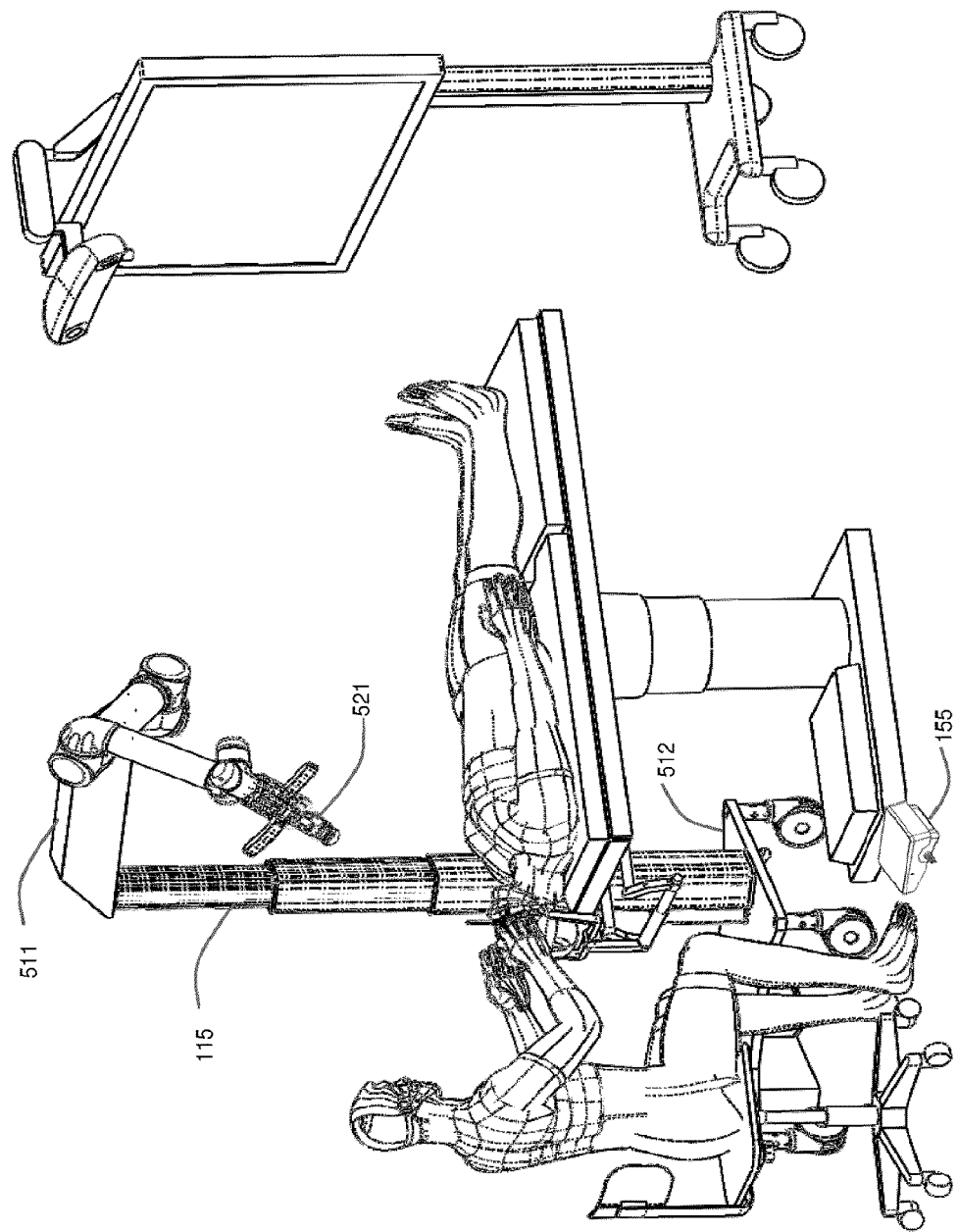
FIGS. 5A-B are exemplary embodiments of an intelligent positioning system including a lifting column.

An intelligent positioning system 250 comprising an automated arm 102, a lifting column 115 and an end effector 104, is placed in proximity to patient 202. Lifting column 115 is connected to a frame of intelligent positioning system 250. As seen in FIG. 1, the proximal end of automated mechanical arm 102 (further known as automated arm herein) is connected to lifting column 115. In other embodiments, automated arm 102 may be connected to a horizontal beam 511 as seen in FIG. 5A, which is then either connected to lifting column 115 or the frame of the intelligent positioning system 250 directly. Automated arm 102 may have multiple joints to enable 5, 6 or 7 degrees of freedom.

End effector 104 is attached to the distal end of automated arm 102. End effector 104 may accommodate a plurality of instruments or tools that may assist surgeon 201 in his procedure. End effector 104 is shown as an external scope, however it should be noted that this is merely an example embodiment and alternate devices may be used as the end effector 104 such as a wide field camera 256 (shown in FIG. 21, microscope and OCT (Optical Coherence Tomography) or other imaging instruments. In an alternate embodiment multiple end effectors may be attached to the distal end of automated arm 102, and thus assist the surgeon in switching between multiple modalities. For example, the surgeon may want the ability to move between microscope, and OCT with stand-off optics. In a further example, the ability to attach a second more accurate, but smaller range end effector such as a laser based ablation system with micro-control may be contemplated.

Figure 2:
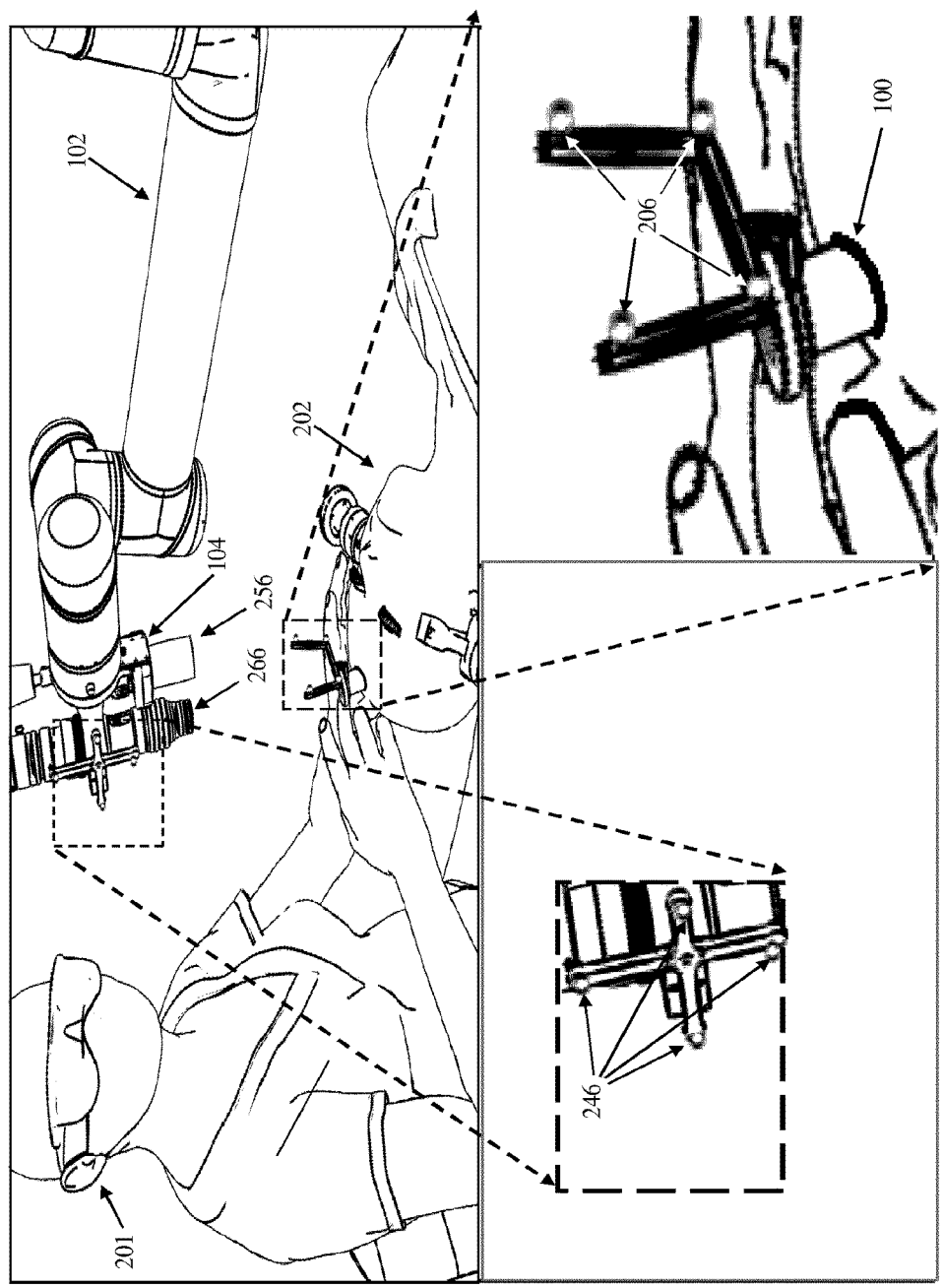
FIG. 2 is an exemplary embodiment illustrating various detailed aspects of a port based surgery as seen in FIG. 1.

The intelligent positioning system 250 receives as input the spatial position and pose data of the automated arm 102 and target (for example the port 100) as determined by tracking system 113 by detection of the tracking markers 246 on the wide field camera 256 on port 100 as shown in FIG. 2. Further, it should be noted that the tracking markers 246 may be used to track both the automated arm 102 as well as the end effector 104 either collectively (together) or independently. It should be noted that the wide field camera 256 is shown in this image and that it is connected to the external scope 266 and the two imaging devices together form the end effector 104. It should additionally be noted that although these are depicted together for illustration of the diagram that either could be utilized independent of the other, for example as shown in FIG. 5A where an external video scope 521 is depicted independent of the wide field camera.

Figure 6A:
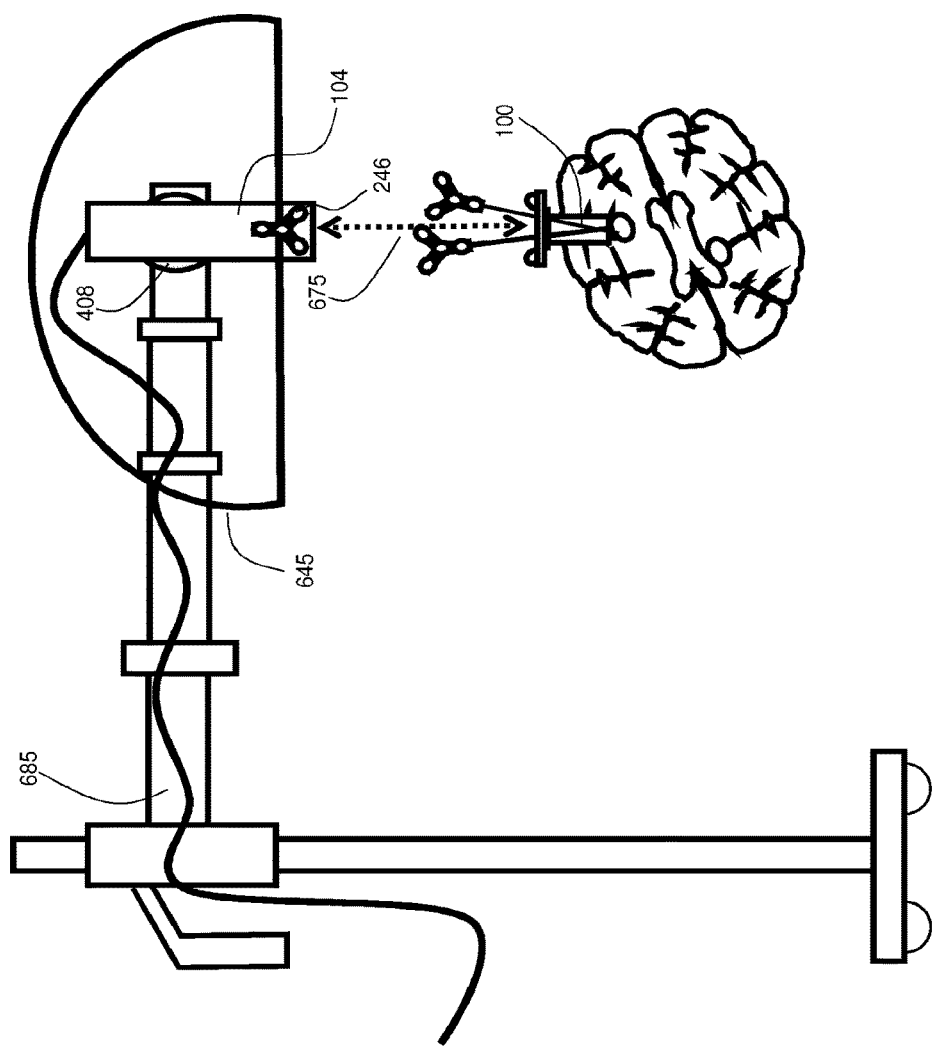
FIGS. 6A-C are exemplary embodiments illustrating alignment of an imaging sensor with a target (port)
Figure 6B:
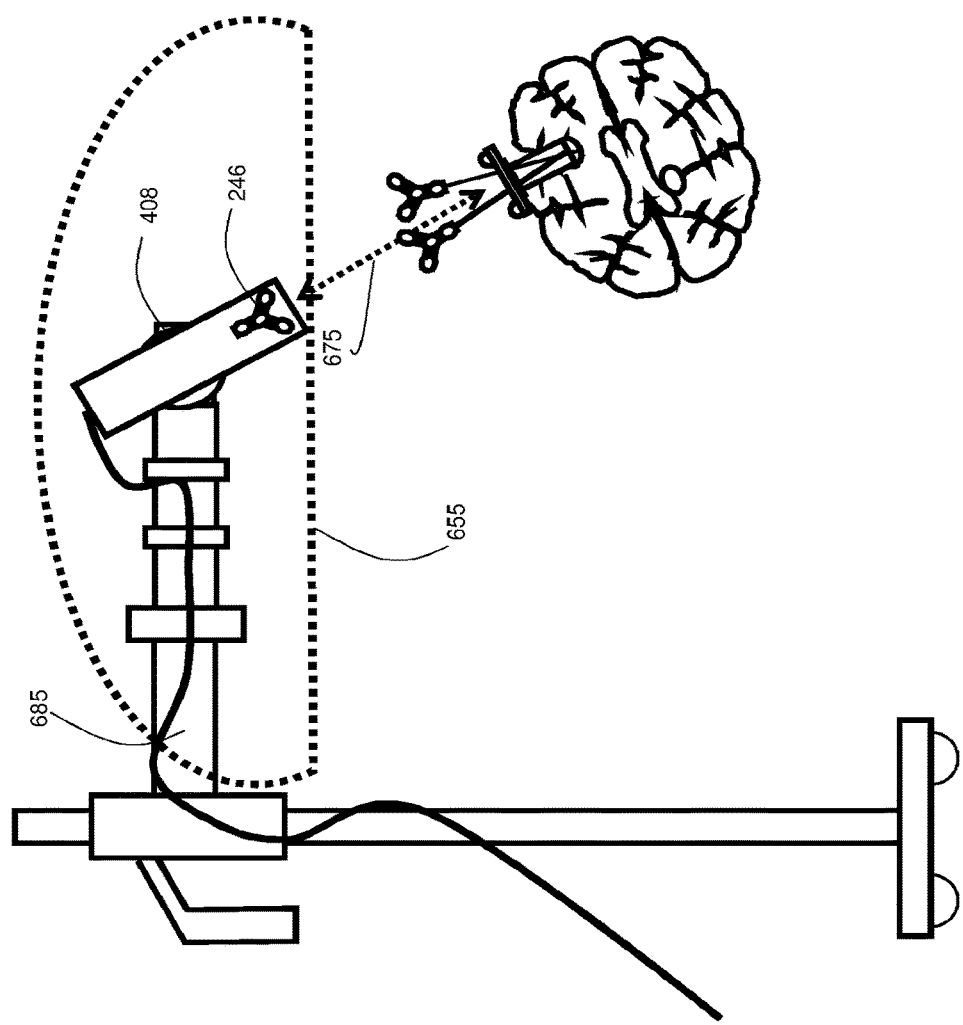

Intelligent positioning system 250 computes the desired joint positions for automated arm 102 so as to maneuver the end effector 104 mounted on the automated arm's distal end to a predetermined spatial position and pose relative to the port 100. This redetermined relative spatial position and pose is termed the "Zero Position" and is described in further detail below and is shown in FIG. 6A-B where the imaging sensor and port are axially aligned 675 having a linear line of sight.

Further, the intelligent positioning system 250, optical tracking device 113, automated arm 102, and tracking markers 246 and 206 form a feedback loop. This feedback loop works to keep the distal end of the port (located inside the brain) in constant view and focus of the end effector 104 given that it is an imaging device as the port position may be dynamically manipulated by the surgeon during the procedure. Intelligent positioning system 250 may also include foot pedal 155 for use by the surgeon 201 to align of the end effector 104 (i.e., a videoscope) of automated arm 102 with the port 100. Foot pedal 155 is also found in FIGS. 5A, 5C and 7. In one example, once the pose of the arm 102 has been acquired by the tracking system, the position of the base of the arm 102 can be computed. From this point forward, the system 250 may align to the instrument attached to the markers 206, 246 as long as the instrument can be tracked; the arm 102 does not need to be tracked again unless the base is moved. The arm 102 may use joint encoders to infer the end effector pose relative to the arm base.

Figure 3:
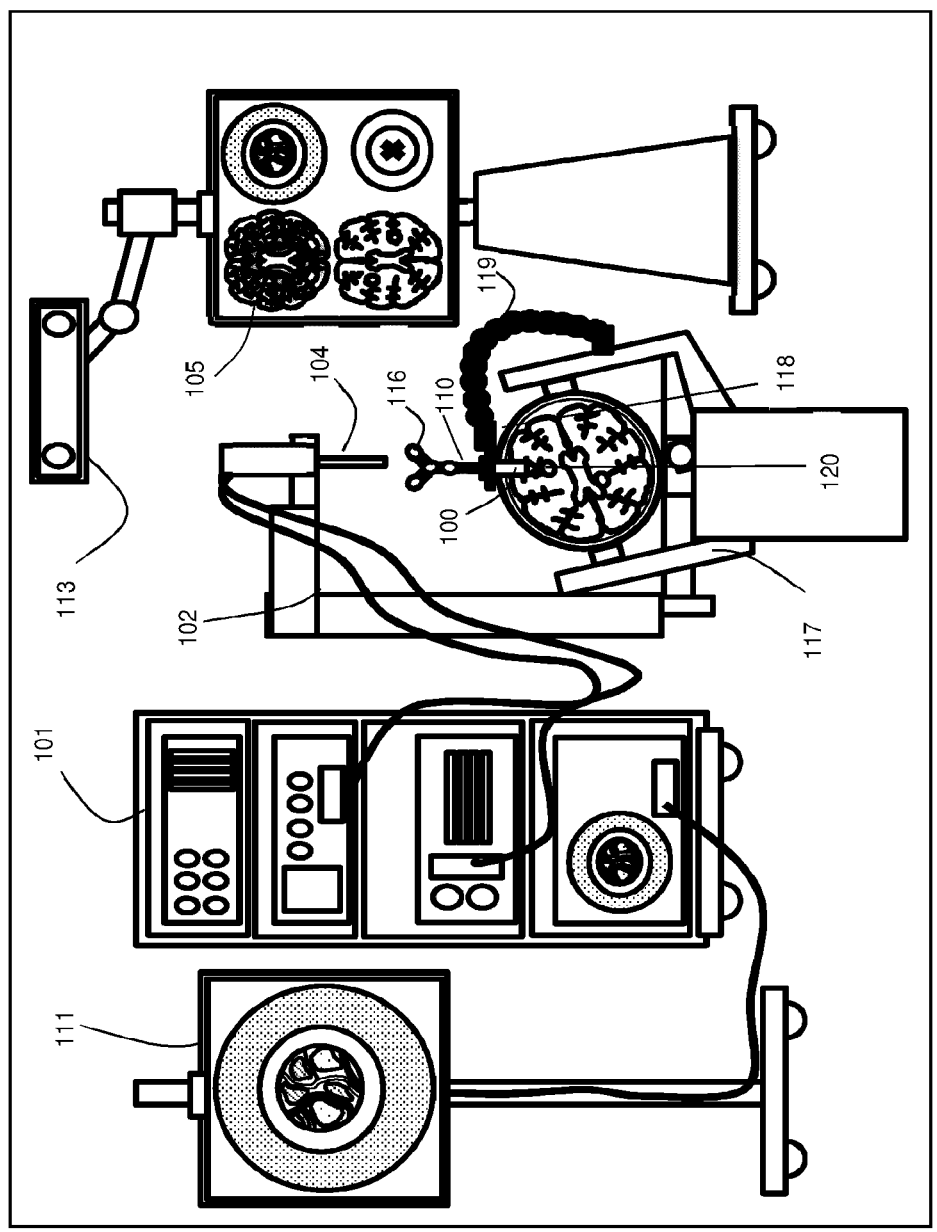
FIG. 3 is an exemplary embodiment illustrating system components of an exemplary navigation system.

FIG. 3 is a diagram illustrating system components of an exemplary navigation system for port-based surgery. In FIG. 3, the main components to support minimally invasive access port-based surgery are presented as separated units. FIG. 3 shows an example system including a monitor 111 for displaying a video image, an optical equipment tower 101, which provides an illumination source, camera electronics and video storage equipment, an automated arm 102, which supports an imaging sensor 104. A patient's brain is held in place by a head holder 117, and inserted into the head is an access port 100 and introducer 1600 as shown in FIG. 16A. The introducer 1600 may be replaced by a tracking probe (with attached tracking marker 116) or a relevant medical instrument such as 1612 used for port-based surgery. The introducer 1600 is tracked using a tracking system 113, which provides position and orientation information for tracked devices to the intelligent positioning system 250.

Figure 16C:
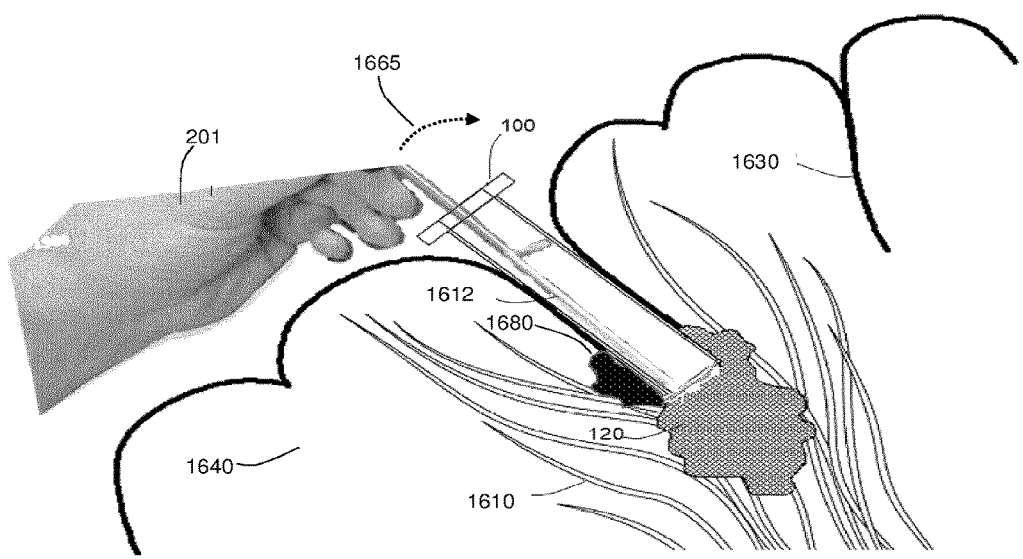
Figure 16D:
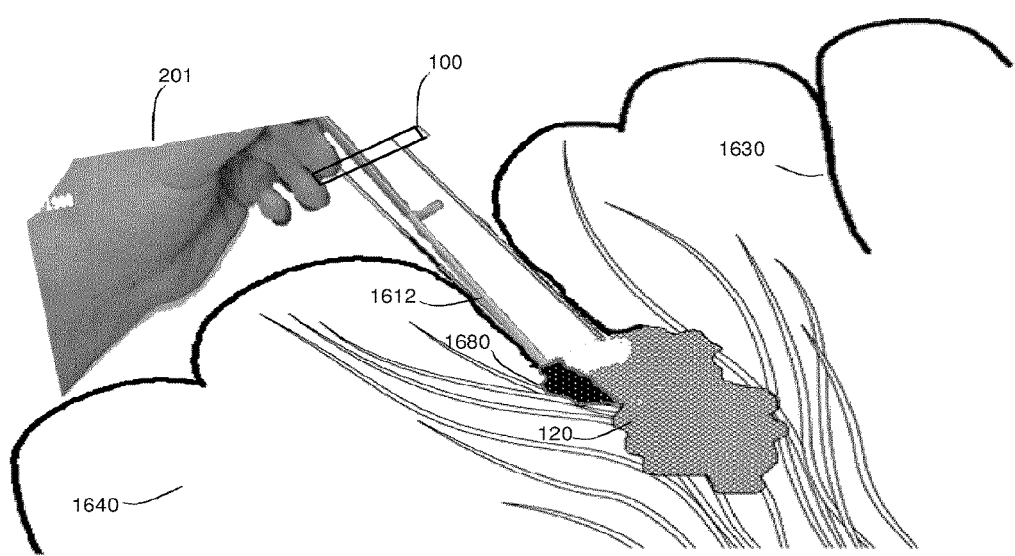

An example of the surgeon dynamically manipulating the port 100 is shown in FIG. 16D. In FIG. 16C-D, a port based tumor resection is being performed within the brain 1640. The surgeon 201 will typically maneuver the port 100 to actively search for and provide access to as much of the tumor 120 or equivalently unhealthy tissue as possible in order to resect it using a medical instrument 1612. In FIG. 16C there is a section of the tumor 1680 that is not accessible given the positioning of the port 100. In order to access that section of the tumor 1680, the surgeon 201 maneuvers the port 100 through a rotation as shown by the dashed arrow 1665. Now referring to FIG. 16D this maneuvering of the port 100 allows the surgeon 201 to access the previously unaccessible section 1680 of the tumor 120 in order to resect it using the medical instrument 1612.

Arm Description

The method described herein is suitable both for an individual automated arm of a multi-arm automated system and for the aforementioned single automated arm system. The gain in valuable operating time, shorter anesthesia time and simpler operation of the device are the direct consequences of the system according to an exemplary version shown in FIG. 1.

Figure 4B:
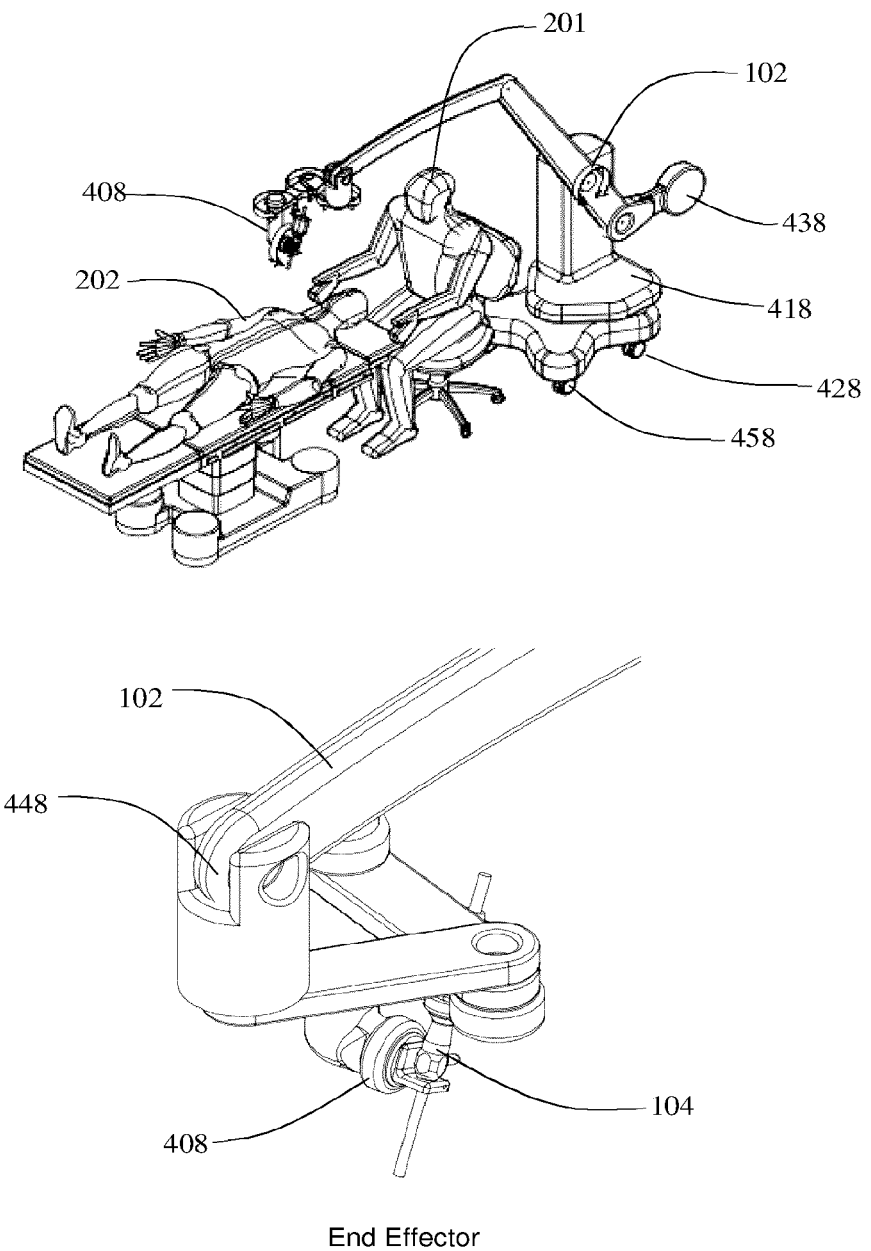
Figure 4C:
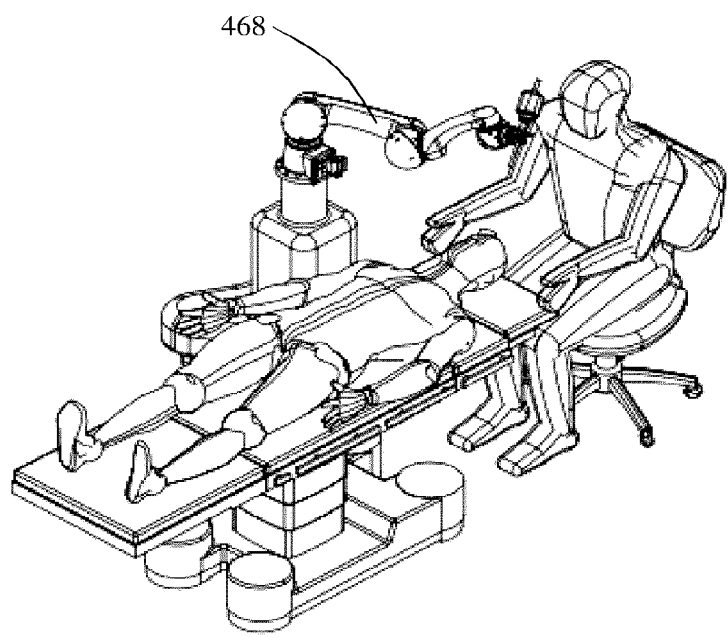
Figure 4C:
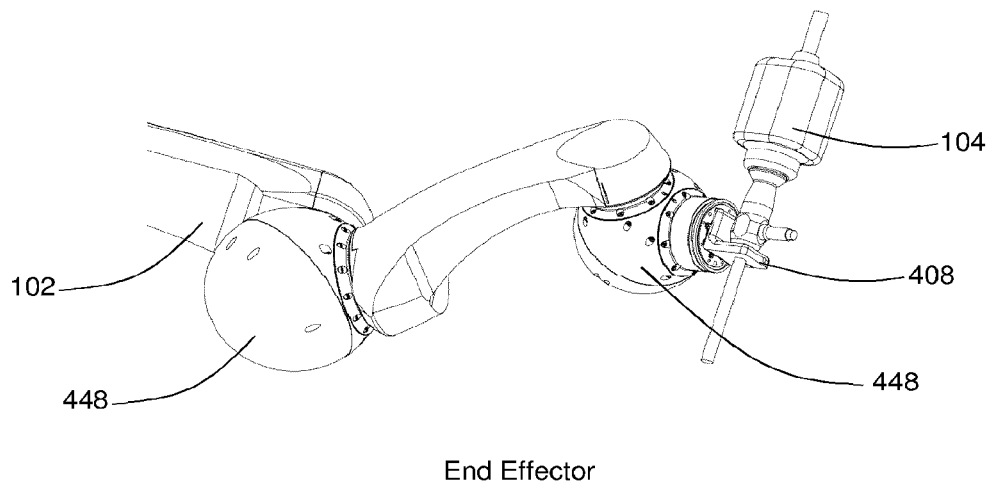

FIGS. 4B and 4C illustrate alternate example embodiments of automated arms. In FIG. 4B the distal end 408 is positioned using an extended automated arm 102 that extends over the surgeon 201. The base 428 of this arm 102 may be positioned away from the patient 202 to provide clear access to the patient 202 lying on the surgical bed. The base 428 may be equipped with caster wheel 458 to facilitate mobility within the operating room. A counter weight 438 may be provided to mechanically balance the system and minimize the load on the actuators (this weight serving the same function as weight 532 in FIG. 5B). The distal end 408 can be arbitrarily positioned due to the presence of a redundant number of degrees of freedom. Joints, such as rotating base 418 in FIG. 4B and joint 448 provide these degrees of freedom. The imaging device 104 may be attached to the final joint or equivalently the distal end 408.

FIG. 4C illustrates another embodiment where a commercially available arm 102 may be used. Again, joints 448 provide redundant number of degrees of freedom to aid in easy movement of the distal end 408. In another embodiment, the distal end may have connectors that can rigidly hold an imaging device while facilitating easy removal of the device to interchange with other imaging devices.

Figure 4D:
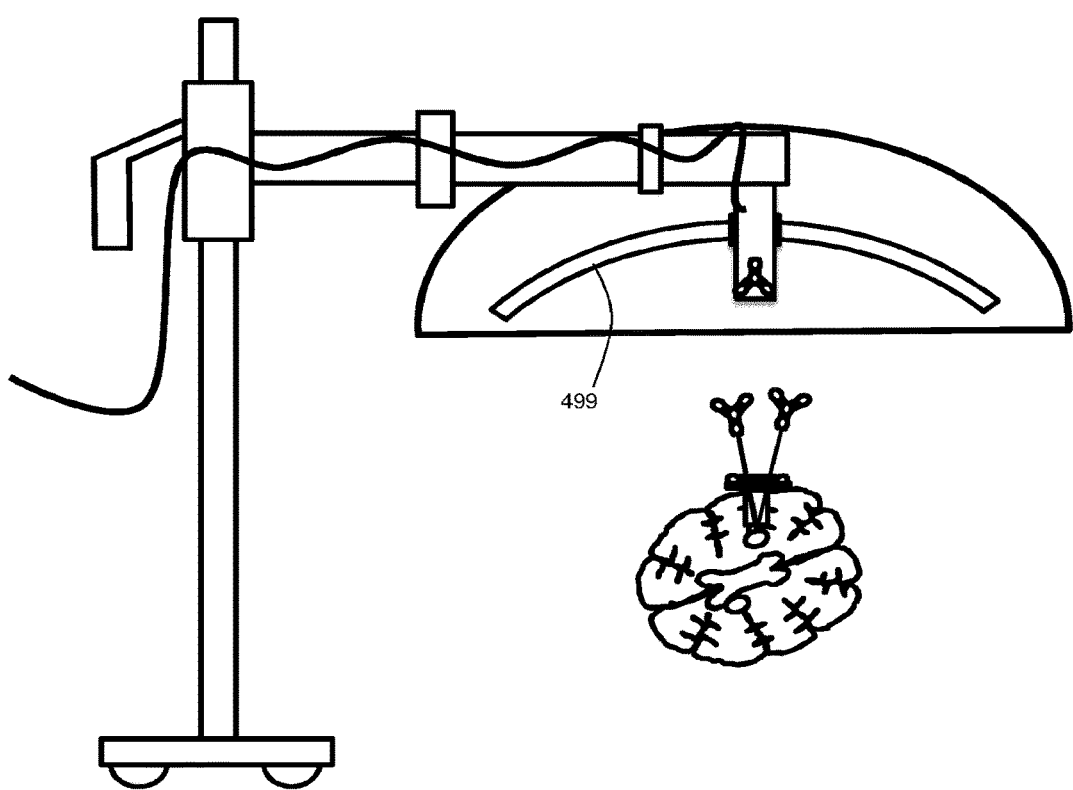

FIG. 4D illustrates an alternative embodiment in which a radial arrangement 499 is employed for the distal end. This arrangement allows the end effector to slide along the curved segment 499 to provide a unique degree of freedom.

It should be noted that while FIGS. 4B-C illustrate a floor-standing design, this embodiment is not intended to limit the scope of the disclosure, and it is to be appreciated that other configurations may be employed. For example, alternative example configurations include a structure that is supported from the ceiling of the operating room; a structure extending from a tower intended to encase imaging instrumentation; and by rigidly attaching the base of the automated arm to the surgical table.

In some embodiments, multiple arms may be used simultaneously for one procedure and navigated from a single system. In such an embodiment, each distal end may be separately tracked so that the orientation and location of the devices is known to the intelligent positioning system and the position and/or orientation of the mounted distal end devices may be controlled by actuating the individual automated arms based on feedback from the tracking system. This tracking can be performed using any of the methods and devices previously disclosed.

In an alternate embodiment, the head of the patient may be held in a compliant manner by a second automated arm instead of a rigid frame 117 illustrated in FIG. 1. The automated head support arm can be equipped with force sensing actuators that provide signals that enable the tracking of minor movement of the head. These sensed position of the head may be provided as feedback to control the relative position of the first automated arm, and correspondingly position the distal end used to mount the device (such as an imaging sensor). This coupling of the head holding assembly and the imaging system may aid in reducing movement artifacts while providing patient comfort. Patient comfort will be greatly enhanced due to the elimination of sharp points used in the traditional head immobilization systems.

In current surgical procedures, available operating room space around the patient being operated on is a scarce commodity due to the many personnel and devices needed to perform the surgery. Therefore the space required by the device around the surgical bed being minimized is optimal.

In an embodiment the space required by the automated arm may be minimized compared to presently used surgical arms through the use of a cantilevered design. This design element allows the arm to be suspended over the patient freeing up space around the patient where most automated arms presently occupy during the surgical procedures. FIG. 5(*a*) shows such a cantilevered arm 511, where the arm anchor is a weighted base 512. This allows the arm to be suspended with minimized risk of tipping, as the weighted base offsets the arm.

Figure 4E:
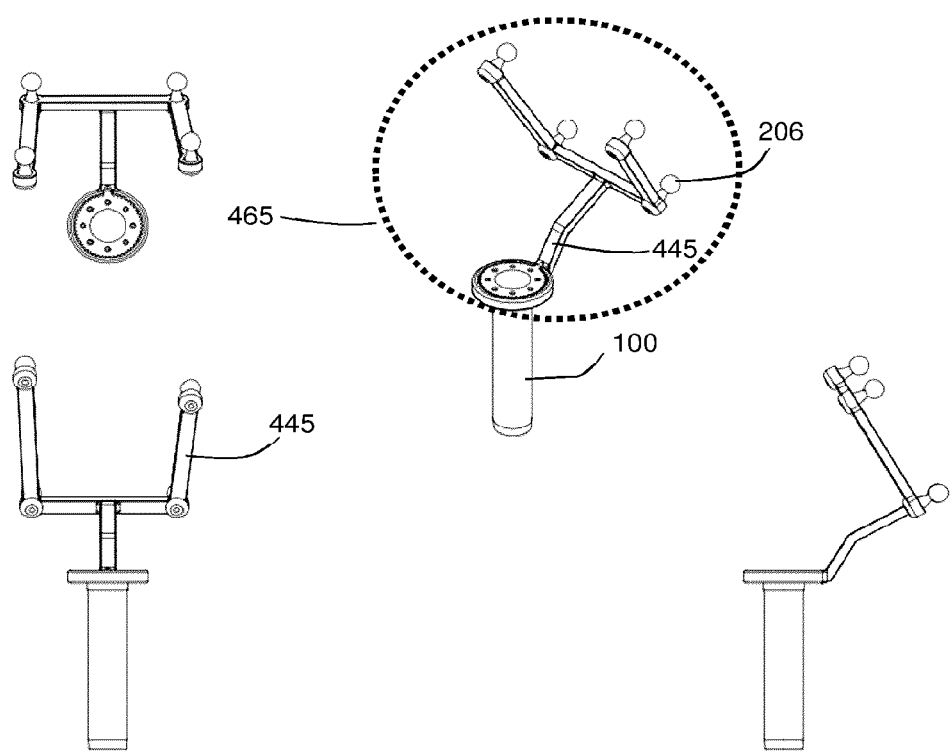
Figure 5B:
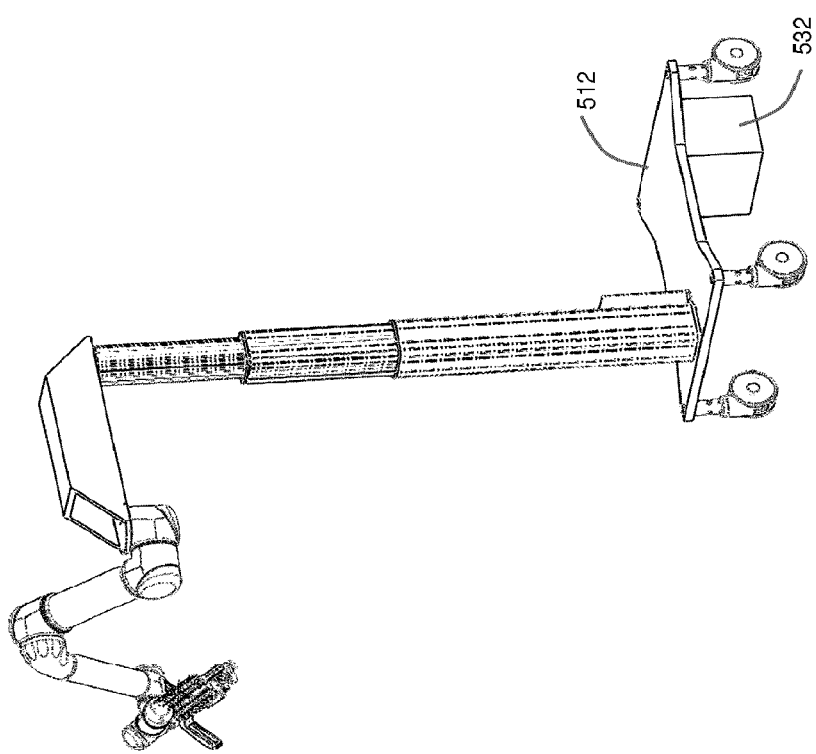

In another embodiment the space required by the automated arm may be minimized compared to presently used surgical arms through the use of a concentrated counterweight 532 attached to the base of the automated arm 512, which takes up a small footprint not only in its height dimension but as well as the floor area in which it occupies. It should be noted that the reduction in area used in the height direction is space that can be occupied by other devices or instruments in the OR such as a surgical tool table. In addition the smaller area required by the base of this automated arm can allow for less restricted movement of personnel around the patient as well as more supplementary device and instruments to be used. FIG. 5B shows such a base which utilizes minimum space and has a concentrated weight 532. The automated arm in this example is held at a particular height by a lifting column 115, as this design requires minimal space. In addition some alternate embodiments that could be used for the lifting column 115 include a 4-bar arm, a scissor lift and pneumatic pistons Tracking In an embodiment as illustrated in FIG. 2 and FIG. 4E, tracking markers 206 may be fitted to port 100. The spatial position and pose of the port (target) are determined using the tracking markers 206 and are then detected by the tracking device 113 shown in FIG. 1 and registered within a common coordinate frame. From the spatial position and pose of the port 100 (target), the desired position of the end effector 104 and the automated arm 102 may be determined. As shown as FIG. 7, lifting column 115 may raise or lower automated arm 102 from an actual position 700 to a desired position 710. For this purpose, it is possible, for example, for the tracking markers 246 located on an assembly as shown in FIG. 2 to be fitted on the automated arm 102, so that its spatial position and pose in the operating room (OR) can thus be determined by the tracking device 113 and the intelligent positioning system 250. Further, the automated arms spatial position and pose can also be determined using position encoders located in the arm that enable encoding of joint angles. These angles combined with the lengths of the respective arm segments can be used to infer the spatial position and pose of the end effector 104 or equivalently the imaging sensor (for example the exoscope 521 shown in FIG. 5A) relative to base 512 of intelligent positioning system 250. Given the automated arms base's 512 spatial position and pose is registered to the common coordinate frame.

In an embodiment, passive tracking markers such as the reflective spherical markers 206 shown in FIG. 2 are seen by the tracking device 113 to give identifiable points for spatially locating and determining the pose of a tracked object (for example a port 100 or external scope 521) to which the tracking markers are connected to.

As seen in FIG. 4E, a medical instrument (target) such as port 100 may be tracked by a unique, attached marker assembly 465 which is used to identify the corresponding medical instrument inclusive of its spatial position and pose as well as its 3D volume representation to a navigation system 200, within the common coordinate frame. In FIG. 4E Port 100 is rigidly connected to tracking marker assembly 465 which is used to determine its spatial position and pose in 3D. Typically, a minimum of 3 spheres are placed on a tracked medical instrument or object to define it. In the exemplary embodiment of FIG. 4E, 4 spheres are used to track the target object (port).

The navigation system typically utilizes a tracking system. Locating tracking markers is based, for example, on at least three tracking markers 206 that are arranged statically on the target (for example port 100) as shown in FIG. 2 on the outside of the patient's body 202 or connected thereto. A tracking device 113 as shown in FIG. 1 detects the tracking markers 206 and determines their spatial position and pose in the operating room which is then registered to the common coordinate frame and subsequently stored by the navigation system.

An advantageous feature of an optical tracking device is the selection of markers that can be segmented very easily and therefore detected by the tracking device. For example, infrared (IR)-reflecting markers and an IR light source can be used. Such an apparatus is known, for example, from tracking devices such as the "Polaris" system available from Northern Digital Inc. In a further embodiment, the spatial position of the port (target) 100 and the position of the automated arm 102 are determined by optical detection using the tracking device. Once the optical detection occurs the spatial markers are rendered optically visible by the device and their spatial position and pose is transmitted to the intelligent positioning system and to other components of the navigation system.

In a preferred embodiment, the navigation system or equivalently the intelligent positioning system may utilize reflectosphere markers 206 as shown in FIG. 4E in combination with a tracking device, to determine spatial positioning of the medical instruments within the operating theater. Differentiation of the types of tools and targets and their corresponding virtual geometrically accurate volumes could be determined by the unique individual specific orientation of the reflectospheres relative to one another on a marker assembly 445. This would give each virtual object an individual identity within the navigation system. These individual identifiers would relay information to the navigation system as to the size and virtual shape of the instruments within the system relative to the location of their respective marker assemblies. The identifier could also provide information such as the tools central point, the tools central axis, etc. The virtual medical instrument may also be determinable from a database of medical instruments provided to the navigation system.

Other types of tracking markers that could be used would be RF, EM, LED (pulsed and un-pulsed), glass spheres, reflective stickers, unique structures and patterns, where the RF and EM would have specific signatures for the specific tools they would be attached to. The reflective stickers, structures and patterns, glass spheres, and LEDs could all be detected using optical detectors, while RF and EM could be picked up using antennas. Advantages to using EM and RF tags would include removal of the line of sight condition during the operation, where using optical system removes the additional noise from electrical emission and detection systems.

In a further embodiment, printed or 3-D design markers could be used for detection by the imaging sensor provided it has a field of view inclusive of the tracked medical instruments. The printed markers could also be used as a calibration pattern to provide (3-D) distance information to the imaging sensor. These identification markers may include designs such as concentric circles with different ring spacing, and/or different types of bar codes. Furthermore, in addition to using markers, the contours of known objects (i.e., side of the port) could be made recognizable by the optical imaging devices through the tracking system as described in the paper [Monocular Model-Based 3D Tracking of Rigid Objects: A Survey]. In an additional embodiment, reflective spheres, or other suitable active or passive tracking markers, may be oriented in multiple planes to expand the range of orientations that would be visible to the camera.

In an embodiment illustrating a port used in neurosurgery, as described above is shown by way of example in FIG. 16B, which shows an access port 100 that has been inserted into the brain, using an introducer 1600, as previously described. In the illustration shown in FIG. 16B, the introducer has been removed. The same access port 100 shown in FIG. 4E includes a plurality of tracking elements 206 as part of a tracking marker assembly 465. The tracking marker assembly is comprised of a rigid structure 445 to supports the attachment of a plurality of tracking elements 206. The tracking markers 206 may be of any suitable form to enable tracking as listed above. In some embodiments, assembly 465 may be attached to access port 100, or integrated as part of access port 100. It is to be understood that the orientation of the tracking markers may be selected to provide suitable tracking over a wide range of relative medical instrument positional orientations and poses, and relative imaging sensor positional orientations and poses.

Safety System

A challenge with automated movement in a potentially crowded space, such as the operating room, may be the accidental collision of any part of the automated arm with surgical team members or the patient. In some embodiments, this may be avoided by partially enclosing the distal end 408 within a transparent or translucent protective dome 645 as shown in FIG. 6A that is intended to prevent accidental contact of the end effector 104 or equivalently the imaging sensor 521 with surgical team members or the patient.

Figure 6C:
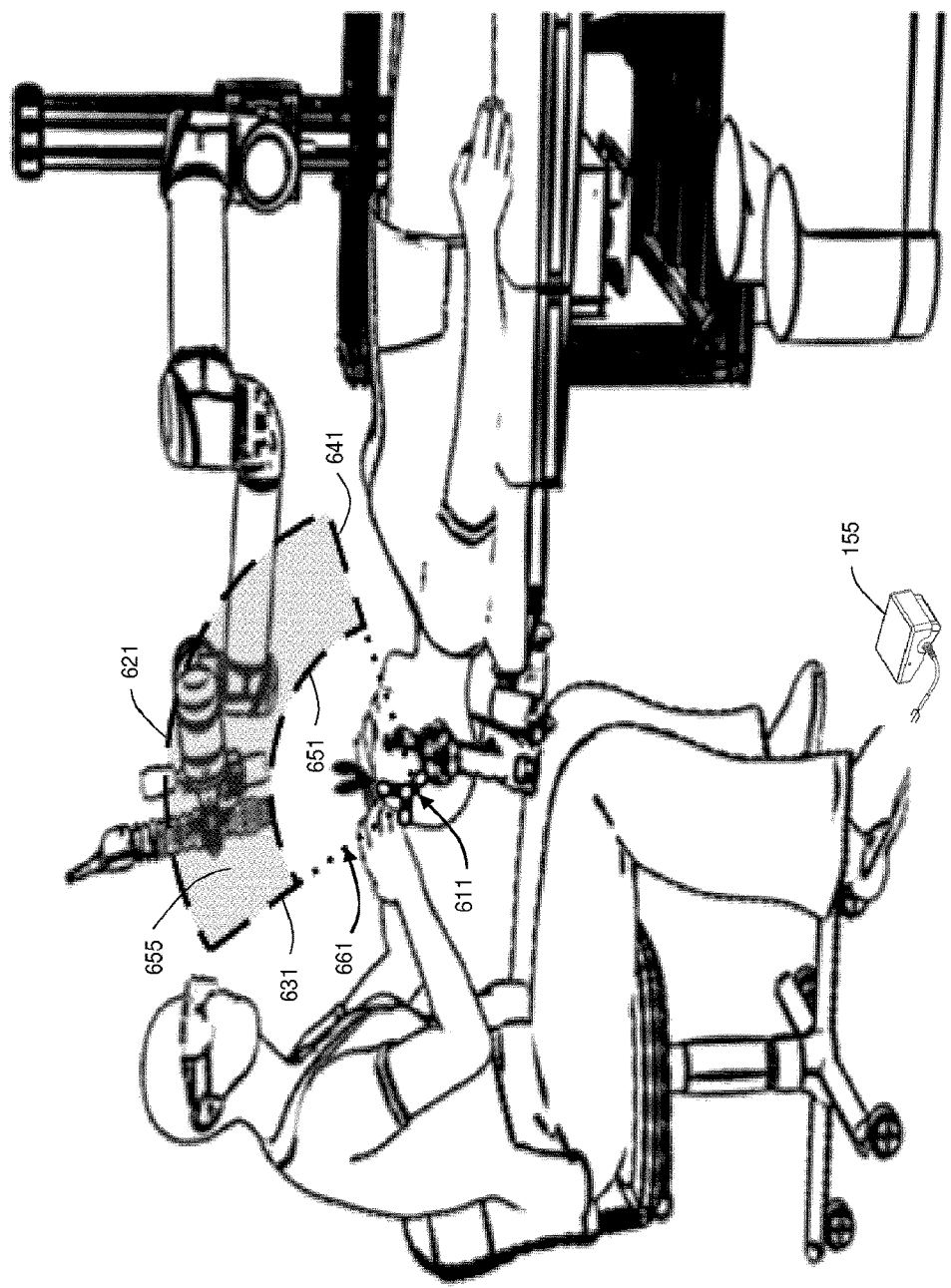

In an alternate embodiment the protective dome may be realized in a virtual manner using proximity sensors. Hence, a physical dome may be absent but a safety zone 655 around the distal end 408 as shown in FIGS. 6B and 6C may be established. In an embodiment this can be accomplished by using proximity sensor technologies to prevent accidental contact between surgical team members and any moving part of the automated arm with mounted imaging sensor. A further embodiment may include a collision sensor to ensure that the moving automated arm does not collide with any object in the environment. This may be implemented using electrical current sensors, force or velocity sensors and/or defined spatial limits of the automated arm.

It should be noted that the safety systems described above are exemplary embodiments of various safety systems that can be utilized in accordance with the intelligent positioning system and should not be interpreted as limiting the scope of this disclosure. In an embodiment the intelligent positioning system is able to acquire the spatial position and pose of the target as well as the automated arm as described above. Having this information the intelligent positioning system can be imposed with a constraint to not position the automated arm within a safety semicircle around the target. In an additional embodiment depicted in FIG. 6C a reference marker 611 can be attached to the patient immobilization frame (117) to provide a reference of the spatial position and pose of the head of the patient, in the common coordinate frame, to the intelligent positioning system through tracking mechanisms described above. Once the position of this reference marker is determined a positional constraint can be imposed on the automated arm effectively defining a "no-fly zone". Given the reference marker 611 has coordinates $(x_r, y_r, z_r, \alpha_r, \beta_r, \gamma_r)$ Where the subscript "r" denotes a coordinate of the reference marker and $\alpha, \beta, \gamma$, are the degree of roll, pitch, and yaw of the marker. Then a new reference origin within the common coordinate frame can be defined by assigning the spatial position of the marker to be the origin and the top, left and right sides of the marker (as determined relative to the common coordinate frame by inferring from the acquired roll, pitch, and yaw) to be the z direction, x direction, and y directions relative to the new reference origin within the common coordinate frame. Given that the position of the end effector on the automated arm is defined in spherical coordinates for example $(r_E, \varphi_E, \theta_E)$ Where the subscript "E" denotes a coordinate of the end effector, a region can be defined in spherical coordinates which can constrain the movement of the end effector to an area 655 outside of which will be defined a "no-fly zone". This can be achieved by defining an angular range and radial range relative to the reference origin which the end effector cannot cross. An example of such a range is shown as follows:

$r_{min} < r_E < r_{max}$ $\varphi_{min} < \varphi_E < \varphi_{max}$ $\theta_{min} < \theta_E < \theta_{max}$ Where the subscripts "min" denotes the minimum coordinate in a particular spherical direction the end effector can occupy and the subscript denotes the maximum coordinate in a particular spherical direction the end effector can occupy. Exemplary radial and angular limit ranges are given for two dimensions as follows and are shown in FIG. 6C as 651 ($r_{min}$) to 621 ($r_{max}$) and 631 ($\varphi_{min}$) to 641 ($\varphi_{max}$) respectively. This embodiment may also be used to define additional constrained regions for example such as those concerned with conserving line of sight of the surgeon, conserving line of sight of the tracking device with the tracking markers on the end effector, and conserving the area in which the surgeon hands will be utilizing the tools. Referring to the port based surgery described above a common acceptable offset range (for example the dotted line 661 defining the length from the reference marker to the beginning of the "fly-zone" shown in FIG. 6C) of the end effector to the target, to allow the surgeon to work comfortably is 20 cm to 40 cm (i.e. in this $r_{min}$=20 cm and $r_{max}$=40 cm).

In another embodiment, a safety zone may be established around the surgical team and patient using uniquely identifiable tracking markers that are applied to the surgical team and patient. The tracking markers can be limited to the torso or be dispersed over the body of the surgical team but sufficient in number so that an estimate of the entire body of each individual can be reconstructed using these tracking markers. The accuracy of modelling the torso of the surgical team members and the patient can be further improved through the use of tracking markers that are uniquely coded for each individual and through the use of profile information that is known for each individual similar to the way the tracking assemblies identify their corresponding medical instruments to the intelligent positioning system as described above. Such markers will indicate a "no-fly-zone" that shall not be encroached when the end effector 104 is being aligned to the access port by the intelligent positioning system. The safety zone may be also realized by defining such zones prior to initiating the surgical process using a pointing device and capturing its positions using the navigation system.

In another embodiment multiple cameras can be used to visualize the OR in 3D and track the entire automated arm(s) in order to optimize their movement and prevent them from colliding with objects in the OR. Such a system capable of this is described by the paper [System Concept for Collision-Free Robot Assisted Surgery Using Real-Time Sensing". Jörg Raczkowsky, Philip Nicolai, Björn Hein, and Heinz Wörn. IAS 2, volume 194 of Advances in Intelligent Systems and Computing, page 165-173. Springer, (2012)]

Additional constraints on the intelligent positioning system used in a surgical procedure include self-collision avoidance and singularity prevention of the automated arm which will be explained further as follows. The self-collision avoidance can be implemented given the kinematics and sizes of the arm and payload are known to the intelligent positioning system. Therefore it can monitor the joint level encoders to determine if the arm is about to collide with itself. If a collision is imminent, then intelligent positioning system implements a movement restriction on the automated arm and all non-inertial motion is ceased.

In an exemplary embodiment given an automated arm with 6 degrees of freedom, the arm is unable to overcome a singularity. As such when a singularity condition is approached the intelligent positioning system implements a movement restriction on the automated arm and all non-inertial motion is ceased. In another exemplary embodiment such as that shown in FIG. 5A an automated arm with six degrees of freedom is provided another degree of freedom by the addition of a lifting column 115. In this case singularities can be overcome as the restricted motion in one joint can be overcome with the movement of another joint. Although this allows the intelligent positioning system to overcome singularities it is a more difficult kinematics problem. An end-effector pose is defined by 3 translational and 3 rotational degrees of freedom; to do the inverse kinematics of a 7DOF manipulator requires that you invert a 6×7 matrix, which is not unique. Therefore, while a 7 degree of freedom manipulator allows you to get around singularities due to this non-uniqueness, it is at an additional computational cost. By adding an extra constraint, like the elbow constrained to stay at a particular height, the system would allow a unique solution to be found which would again ease the computational requirement of the system.

Having the automated arm be mobile for medical flexibility and economic viability, instills another constraint on the intelligent positioning system. This is to ensure either the mobile base 512 is in motion or the automated arm is in motion at any given time. This is accomplished by the system by having an auto-locking mechanism which applies brakes to the base when movement of the arm is required. The reasoning for this constraint is movement of the arm without a static base will result in synonymous motion of the base (basic physics). If the arm is mounted on a vertical lifting column, the lifting column adds to this constraint set: the lifting column cannot be activated if the mobile base wheels are not braked or if the arm is in motion. Similarly, the arm cannot be moved if the lifting column is active. If the mobile base wheel brakes are released, the arm and lifting column are both disabled and placed in a braked state.

Advantages of Arm

Figure 8A:
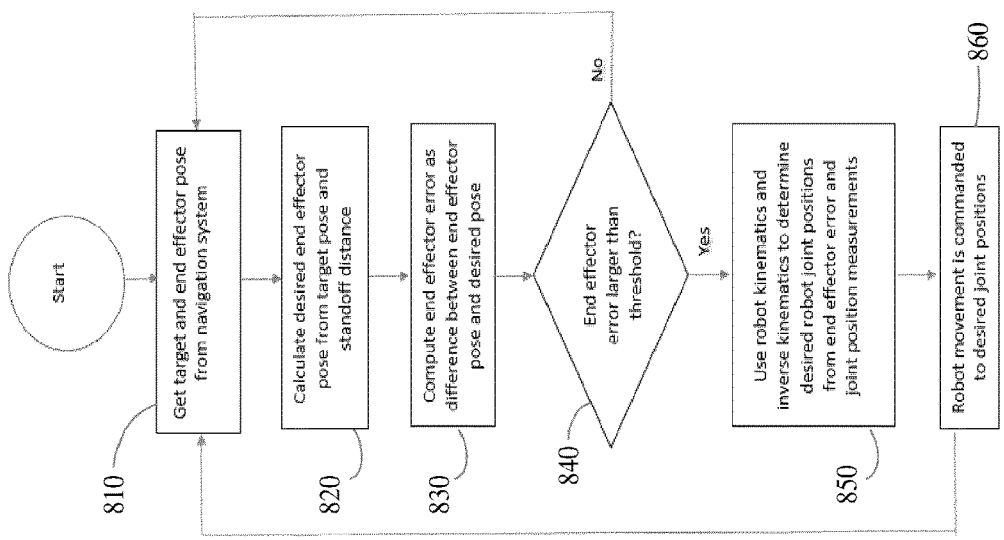
FIG. 8A is a flow chart describing the sequence involved in aligning an automated arm with a target.

In an advantageous embodiment of the system, the automated arm with mounted external scope will automatically move into the zero position (i.e. the predetermined spatial position and pose) relative to the port (target) by the process shown in FIG. 8A. When this is done during the surgical procedure it is possible to start immediately on the treatment of the patient allowing the surgeon to skip the periodic manual step of realigning the external scope with the port.

In the preferred embodiment the chosen position of the automated arm will align the distal end with mounted external scope, to provide the view of the bottom (distal end) of the port (for port based surgery as described above). The distal end of the port is where the surgical instruments will be operating and thus where the surgical region of interest is located. In another embodiment this alignment (to provide the view at the bottom of the port) can be either manually set by the surgeon or automatically set by the system depending on the surgeons' preference and is termed the "zero position". To automatically set the view, the intelligent positioning system will have a predefined alignment for the end effector relative to the port which it will use to align automated arm.

Referring to FIG. 6A which depicts the preferred zero position of the end effector 104 with respect to the port 100. The relative pose of the imaging device (either the external scope 521 or wide field camera 256) is selected such that it guarantees both a coaxial alignment and an offset 675 from the proximal end of the port as shown in both FIGS. 6A-B. More specifically, there ensues a co-axial alignment of the imaging device axis forming, for example, a central longitudinal axis of the imaging device with the longitudinal axis of the port (target) (such as 675 shown in FIG. 6A-B) as predefined by the zero position. This is particularly suitable for cases such as the port based surgery method mentioned above for tumor resection, as well as Lumbar Microscopic Discectomy and Decompression as it allows the port to be viewed from the optimal angle resulting in the largest field of view for the surgeon, where the surgeon will be manipulating their surgical instruments to perform the surgery. For example, as is described above and illustrated in FIGS. 16A, 16B, and 16C. A co-linear alignment would provide the optimal view given the imaging devices' line of sight is normal to the plane of the region of interest, preventing occlusion by the ports walls which would occur in alternate lines of sight.

Manual/Semi-Manual Automated Arms

The example embodiment of the automated arms shown in FIGS. 6A and 6B and described in the prior paragraph, are shown supporting an external imaging device having tracking markers 246 attached thereto. In these figures, a floor mounted arm is shown with a large range manipulator component 685 that positions the end effector of the automated arm (for example, with 6 degrees of freedom), and has a smaller range of motion for the positioning system (for example, with 6 degrees of freedom) mounted on distal end 408. As shown in FIG. 6A, the distal end of the automated arm 408 refers to the mechanism provided at the distal portion of the automated arm, which can support one or more end effectors 104 (e.g. imaging sensor). The choice of end effector would be dependent on the surgery being performed.

Alignment of the end effector of the automated arm is demonstrated in FIGS. 6A-B. When the access port is moved, the system detects the motion and responsively repositions the fine position of the automated arm to be co-axial 675 with the access port 100, as shown in FIG. 6B. In a further embodiment, the automated arm may maneuver through an arch to define a view that depicts 3D imaging. There are 2 ways to do this—1) is to use two 2D detectors at known positions on the arm, or use one 2D detector and rock back and forth in the view (or move in and out).

Alignment

Figure 7:
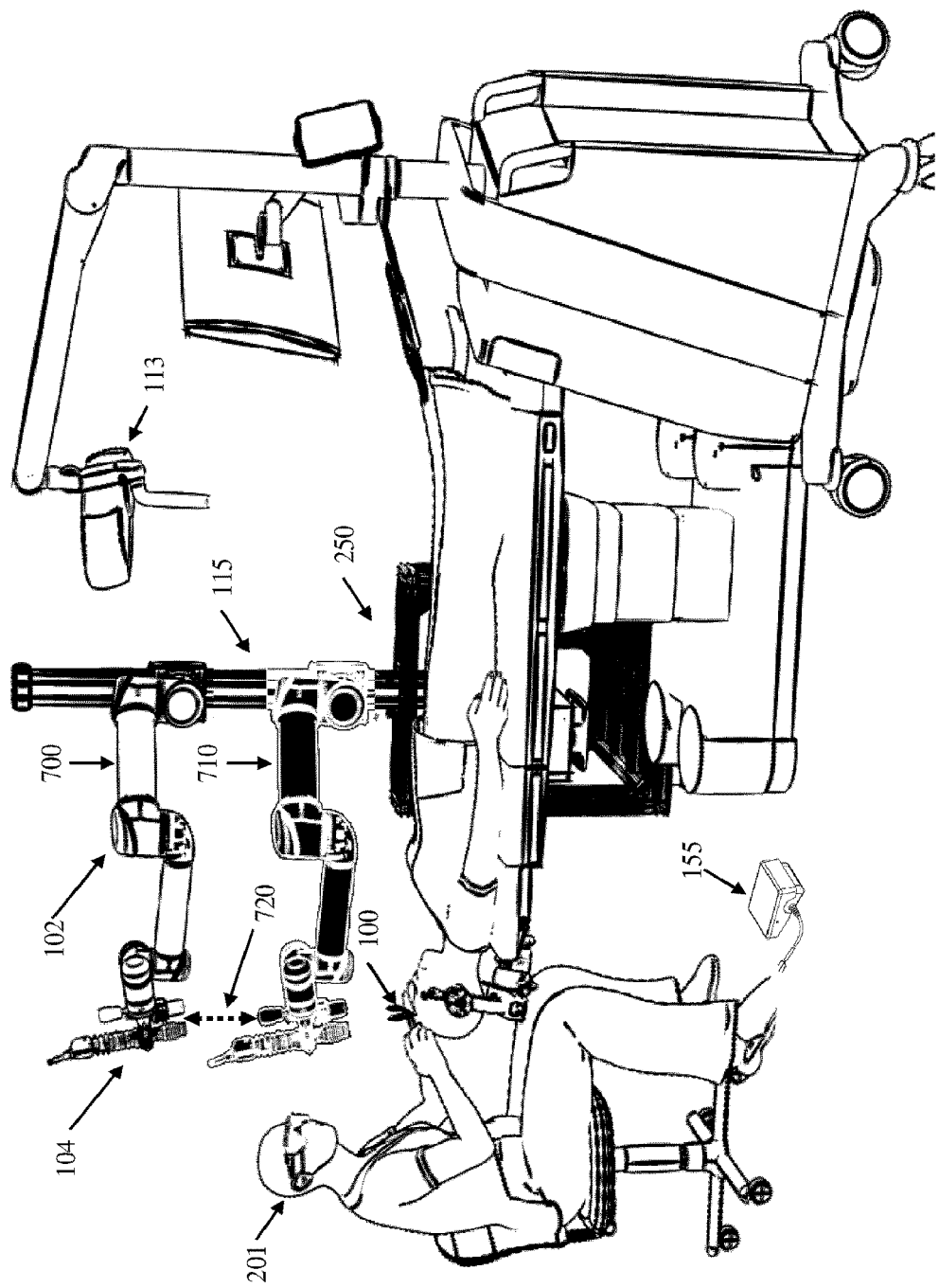
FIG. 7 is an exemplary embodiment of an alignment sequence implemented by the intelligent positioning system.

FIG. 8A is a representation of an alignment sequence implemented by the intelligent positioning system. In FIG. 7, the automated arm 102 may be moved from its actual position 700 into its desired position 710 with the aid of a cost minimization algorithm or equivalently an error minimization method by the intelligent positioning system 250.

In FIG. 7, the actual position 700 of the automated arm 102 is acquired continually. The automated arm achieves the desired alignment (zero position) with the target (port 100) through movement actuated by the intelligent positioning system. The intelligent positioning system 250 requires the actual position 700 of the arm 102 to approximate the desired position of the arm 710 as depicted by arrow 720 in FIG. 7. This approximation occurs until the position of the actual arm alignment approximates that of the desired alignment (zero position) within a given tolerance. At the desired alignment 710, the automated arm 102 mounted with the imaging device 104 is then in the zero position with respect to the target (port 100). The subsequent alignment of the automated arm 102 into the desired position 710 relative to the port 100 may be actuated either continuously or on demand by the surgeon 201 through use of the foot pedal 155.

The cost minimization method applied by the intelligent positioning system is described as follows and depicted in FIG. 8A. In an embodiment visual serving is executed in a manner in which tracking device(s) 113 are used to provide an outer control loop for accurate spatial positioning and pose orientating of the distal end of the automated arm 102. Where imaging device 104 may be attached. The Intelligent positioning system also utilizes this open control loop to compensate for deficiencies and unknowns in the underlying automated control systems, such as encoder inaccuracy.

FIG. 8A is an exemplary flow chart describing the sequence involved in aligning an automated arm with a target using a cost minimization method. In the first step (810) the end effectors spatial position and pose is determined, typically in the common coordinate frame, through the use of the tracking device or another method such as the template matching or SIFT techniques described in more detail below. In the next step (820), the desired end effector spatial position and pose is determined with the process 1150 shown in FIG. 11 and described further below.

The pose error of the end effector as utilized in step (830), is calculated as the difference between the present end effector spatial position and pose and the desired end effector spatial position and pose and is shown as arrow distance 720 in FIG. 7. An error threshold as utilized in step (840) is determined from either the pose error requirements of the end effector or the automated arm limitations. Pose error may include resolution of the joints, minimizing power, or maximizing life expectancy of the motors. If the pose error of the end effector is below the threshold, then no automated arm movement is commanded and the intelligent positioning system waits for the next pose estimation cycle. If the pose error is greater than the threshold the flow chart continues to step (850) where the end effector error 720 is determined by the intelligent positioning system as a desired movement. The final step (860) requires the intelligent positioning system to calculate the required motion of each joint of the automated arm 102 and command these movements. The system then repeats the loop and continuously takes new pose estimations from the intelligent positioning system 250 to update the error estimation of the end effector spatial position and pose.

Alignment Flow Chart

Figure 8B:
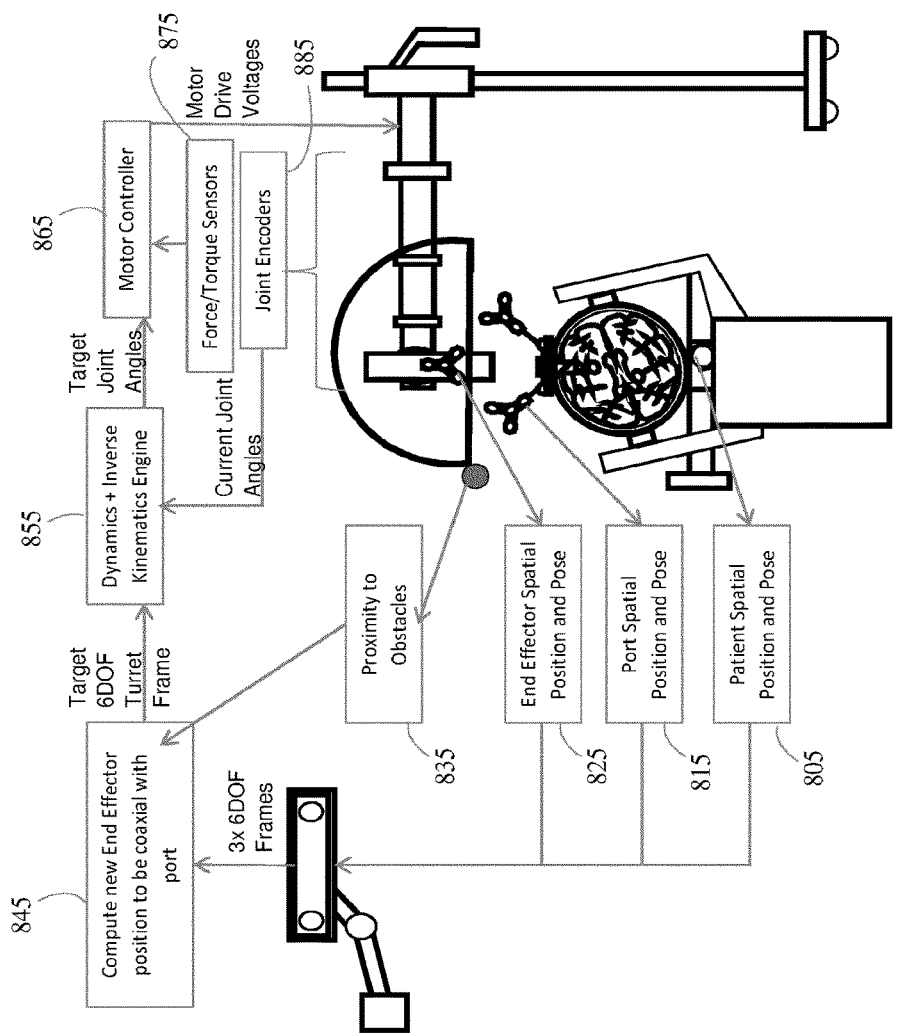
FIG. 8B is a flow chart describing the sequence involved in aligning an automated arm with a target.
Figure 10B:
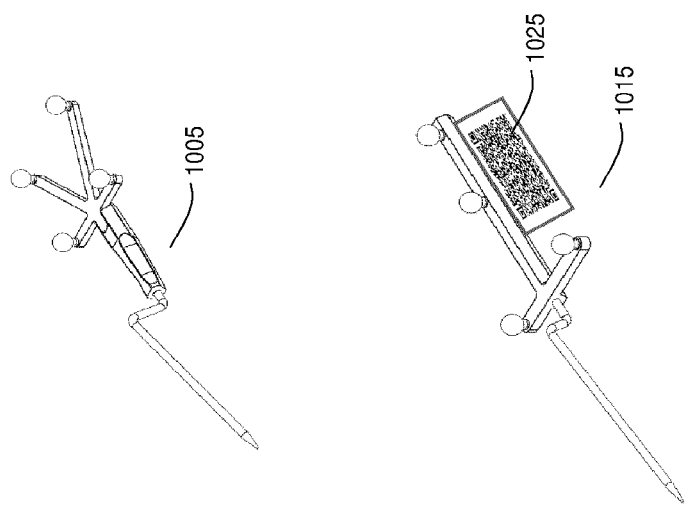

In an embodiment the intelligent positioning system can perform the alignment of the automated arm relative to the port optimized for port based surgery using the method as described by the flow chart depicted in FIG. 8B. FIG. 8B describes the method implemented in the flow chart in FIG. 8A in a refined version as used in the port based surgery described above. In FIG. 8B, an exemplary system diagram is shown illustrating various component interactions for tracking of the access port (target) by the automated arm supporting an imaging device. Tracking and alignment may be triggered manually by the surgeon, or set to track continuously or various other types of automated arm alignment modes as described below in further detail. In both given example modes, the operational flow may be performed as follows:

1. The tracking device(s) transmits the spatial positions and poses of the access port patient and end effector, analogous to step 810 in FIG. 8A, to the intelligent positioning system after which they are registered to the common coordinate frame. The coordinates in this step are given for the port, the patient, and the end effector as 815, 805, and 825 as shown in FIG. 8B respectively.
2. If, for example, the imaging sensor is to be continuously (i.e. in real time) aligned relative to the access port at the zero position as described below (in the common coordinate frame), a new desired spatial position and pose for the end effector (mounted with the imaging sensor) including the zoom, and focus of the camera is calculated which is shown as step (845) in FIG. 8B and is analogous to 820 in FIG. 8A, as described above. In an embodiment the zero position is one that will orient the imaging device coaxially with the access port during a port based surgery as described in more detail below in the description of FIG. 15. If, alternatively, the end effector is continuously aligned relative to a medical instrument for example the surgical pointer tools 1015 and 1005 as shown in FIG. 10B, the same calculations are computed to orient the imaging sensor such that the focal point is aimed at the tip of the medical instrument or aligned relative to it in a predetermined (by the process described in FIG. 11) zero position.
3. In the next step (855), analogous to step 850 in FIG. 8A, of the process the intelligent positioning system (using an inverse kinematics engine) reads the current joint positions of the automated arm and computes offset joint positions for the automated arm that would achieve the desired spatial position and pose of the end effector as defined by the zero position.
4. The intelligent positioning system then drives the joints to the desired joint angles via a motor controller (865) contained in the intelligent positioning system, this step is analogous to step 860 in FIG. 8A. Inputs into the motor controller include the joint encoders (885) located in the automated arm as well as any connected (i.e. to the intelligent positioning system) force/torque sensors 875. It will be understood that various strategies can be used for the determination of the trajectory of the automated arm. Some examples are: straight line path of the distal end frame, equal joint speed, and equal joint travel time. If the location and geometry of other equipment in the vicinity of the arm are known.
5. During the execution of the automated arm trajectory, one or more gauges, sensors or monitors (such as motor current, accelerometers and or force gauges) may be monitored to halt the arm in the case of collision. Other inputs to prevent a collision include proximity sensors that would give information (835) on the proximity of the automated arm relative to obstacles in the automated arms vicinity as well as defined "no-fly zones" 655 depicted in FIGS. 6B-C and described herein.

Because the surgical arena is filled with many pieces of equipment and people, it may be desirable that all gross-alignment of the distal end is performed manually and only the fine adjustment is performed automatically from tracked data.

Constant realignment of an end effector with a moving target during a port based surgery is problematic to achieve as the target is moved often and this can result in increased hazard for the equipment and personnel in the surgical suite. Movement artefacts can also induce motion sickness in the surgeons who constantly view the system. There are multiple embodiments that can deal with such a problem two of which will be described further. The first involves the intelligent positioning system constraining the arm movement so that it only realigns with the target if the target has been in a constant position, different from its initial position, for more than a particular period of time. This would reduce the amount of movement the arm undergoes throughout a surgical procedure as it would restrain the movement of the automated arm to significant and non-accidental movements of the target. Typical duration for maintaining constant position of the target in port based brain surgery is 15 to 25 seconds. This period may vary for other surgical procedures even though the methodology is applicable. Another embodiment may involve estimation of the extent of occlusion of the surgical space due to misalignment of the port relative to the line of sight of the video scope 104. This may be estimated using tracking information available about the orientation of the port and the orientation of the video scope. Alternatively, extent of occlusion of the surgical space may be estimated using extent of the distal end of the port that is still visible through the video scope. An example limit of acceptable occlusion would be 0-30%.

The second embodiment is the actuation mode described herein. Alternate problems with constant realignment of the end effector can be caused by the target as it may not be so steadily placed that it is free of inadvertent minuscule movements that the tracking system will detect. These miniscule movements may cause the automated arm to make small realignments synchronous with small movements of the port. These realignments can be significant as the end effector may be realigning in a radially manner to the port and hence a small movement of the target may be magnified at a stand-off distance (i.e. angular movements of the target at the location of the target may cause large absolute movements of the automated arm located at a radial distance away from the target). A simple way to solve this problem is to have the intelligent positioning system only actuate movement of the arm, if the automated arm's realignment would cause the automated arm to move greater than a threshold amount. For example a movement which was greater than five centimeters in any direction.

Automatic Alignment

As described above, one aspect of the present description provides a medical navigation system (e.g., the navigation system 200) having a computing device such as the control and processing system 1400 having a processor 1402 coupled to a memory 1404, a tracking camera for tracking medical devices (e.g., intelligent positioning system 1440 including tracking device 113) and a display for displaying an image (e.g., display 111). The medical navigation system further has an automated arm assembly (e.g., automated arm 102) electrically coupled to the computing device and controlled by a signal provided by the computing device. The automated arm assembly includes a multi-joint arm having a distal end connectable to an effector (e.g., the end effector 104) that supports a surgical camera (e.g., which may be attached to or part of the scope 266) electrically coupled to the computing device. The medical navigation system further has a medical device having a tracking marker (e.g., the tracking markers 206 and/or 246) attachable to the medical device. The computing device may be configured to position the automated arm assembly, based on an input command, in response to a position in space of the medical device such that a surgical site of interest remains within a field of view of the surgical camera. The position in space of the medical device may be determined by the computing device based on a signal provided to the computing device by the tracking camera. The computing device may be further configured to display on the display 111 an image provided by an image signal generated by the surgical camera.

In one example, the input command may be provided by any one of the foot pedal 155, a joystick, a microphone receiving a voice instruction, a transducer detecting a gesture, or a wireless electronic device that may be configured to act as a remote control to the computing device.

In one example, the medical device may be a pointer or an access port, such as the port 100. The surgical site of interest may be a pointing end of the pointer when a pointer is used as the medical device or an axial view down a longitudinal axis of the access port 100, when the access port 100 is the medical device.

In one example, the computing device may be further configured to track both the pointer and the access port concurrently and the surgical site of interest may be dynamically selectable, for example by the surgeon using an input device coupled to the medical navigation system 200.

The computing device may be further configured to control the surgical camera to perform autofocus on the surgical site of interest whenever the automated arm assembly is moved, for example as described in more detail below in connection with FIG. 17.

The computing device may further have a foot pedal, such as the foot pedal 155, coupled to the computing device and a zoom level of the surgical camera may be controlled by input provided to the computing device from the foot pedal, such as by the surgeon 201 depressing buttons on the foot pedal 155.

As described in detail above in connection with FIG. 8B, automatically moving the automated arm assembly may include a number of steps, such as: (a) identifying the surgical site of interest in a predetermined coordinate frame, where the surgical site of interest based on a position and an orientation of the medical device; (b) obtaining a position and an orientation for the effector on the automated arm, where the position and orientation are defined in the predetermined coordinate frame; (c) obtaining a desired standoff distance and a desired orientation between the surgical site of interest and the effector; (d) determining a new desired position and a new desired orientation for the effector from the position and orientation of the surgical site of interest and the desired standoff distance and the desired orientation; and (e) moving the effector to the new position and orientation.

The computing device may further have a foot pedal, such as the foot pedal 155, coupled to the computing device and the automated arm assembly may move only when input is received from the foot pedal. In other words, as a safety feature, the automated arm assembly may remain stationary except when the surgeon 201 presses a button on the foot pedal 155, at which time the automated arm assembly may move into proper position based on the current position in space of the medical device being tracked. While the example of a foot pedal 155 is used, any suitable input device may be used to meet the design criteria of a particular application, including any input device mentioned herein.

The computing device may further be configurable such that automatic movement of the automated arm assembly includes at least three modes. In the first mode, the surgical camera may automatically align to a longitudinal axis and a rotation of the access port 100. In a second mode, the surgical camera may automatically align to the longitudinal axis only of the access port, so that rotation of the access port 100 about its axis does not cause movement of the automated arm since the surgical site of interest has not shifted in space in this instance. In a third mode, the surgical camera may automatically align to a point of interest on a medical device, such as the tip of a pointer, so that the surgical camera simply follows a point on the medical device in space.

In one example, the effector may further support a light source and automatically moving the automated arm assembly in response to a position in space of the medical device such that the surgical site of interest remains within a field of view of the surgical camera also ensures that the surgical site of interest remains illuminated since the light source moves with the surgical camera.

The effector may further have a tracking marker (e.g., tracking markers 246) attached to the effector and the automated arm assembly may automatically move such that a desired standoff distance between the surgical camera and the surgical site of interest is maintained. In other words, computing device may control the automated arm assembly to ensure a constant minimum clearance between the scope 266, camera 256, arm 102 and the patient 202 such as not to interfere with the workspace of the surgeon 201. In one example, the surgical camera may include the video scope 266 and the medical device may have at least three optical tracking markers 206 attachable to the medical device.

Another aspect of the present description contemplates a method for use in a medical navigation system (e.g., the navigation system 200) having a computing device (e.g., control and processing system 1400) including a processor (e.g., processor 1402) coupled to a memory (e.g., memory 1404), a tracking camera (e.g., intelligent positioning system 1440 including tracking device 113) for tracking medical devices, and a display (e.g., display 111) for displaying an image. The medical navigation system may further include an automated arm assembly (e.g., the automated arm 102) electrically coupled to the computing device and controlled by a signal provided by the computing device, where the automated arm assembly includes a multi-joint arm having a distal end connectable to an effector (e.g., the end effector 104) that supports a surgical camera (e.g., which may be part of or attached to the scope 266) electrically coupled to the computing device. The method includes positioning the automated arm assembly, based on an input command, in response to a position in space of a medical device such that a surgical site of interest remains within a field of view of the surgical camera. The position in space of the medical device may be determined by the computing device based on a signal provided to the computing device by the tracking camera. The method may further include displaying on the display 111 an image provided by an image signal generated by the surgical camera. The method may include some or all of the features described above with regards to the automatic alignment of the medical navigation system.

Template Matching and Sift Alignment Technique

An alternate method of aligning the port is to use machine vision applications to determine the spatial position and pose of the port from the imaging acquired by the imaging sensor. It should be noted that these techniques (i.e. template matching and SIFT described below) can be used as inputs to step (810) in the flow chart depicted in FIG. 8A and described in detail above, as opposed to the optical tracking devices described above.

The mentioned methods utilize a template matching technique or in an alternate embodiment a SIFT Matching Technique to determine the identity, spatial position, and pose of the target, relative to the end effector mounted on the automated arm. In one embodiment the template matching technique would function by detecting the template located on the target and inferring from its skewed, rotated, translated, and scaled representation in the captured image, its spatial position and pose relative to the imaging sensor.

FIGS. 10A and 10B are illustrations depicting target characteristics that can be utilized in optical detection methods. The FIGS. 10A and 10B contain two targets the first being a surgical pointer tool 1015 and the second being a port 100 both having attached templates 1025 and 1030 respectively. In an alternate detection method the SIFT technique functions by using a known size ratio of two or more recognizable features of a target to analyze an image obtained by an imaging sensor to detect the target. For example as shown in FIG. 10A, the features could be the inner 1020 and outer circumference 1010 contours of the lip of the port 100. Once the feature is identified the SIFT technique uses the features' skewed, rotated, translated, and scaled representation in the analyzed image to infer its spatial position and pose relative to the imaging sensor. Both the SIFT Matching and Template Matching Techniques are described in detail by the paper [Monocular Model-Based 3D Tracking of Rigid Objects: A Survey]. It should be noted that other 3D Tracking methods can be used to determine the identity, spatial position, and pose of a target relative to an imaging sensor through analyzing the imaging obtained by the imaging sensor such as described throughout the mentioned paper [Monocular Model-Based 3D Tracking of Rigid Objects: A Survey, section 4].

Manual/Semi Manual Flow

In further implementations of an intelligent positioning system, both manual and automatic alignment of the automated arm may be achieved using the same mechanism through use of force-sensing joints in the automated arm that would help identify intended direction of motion as indicated by the user (most likely the surgeon and surgical team). The force sensors embedded in the joints can sense the intended direction (e.g. pull or push by the user (i.e. surgical team or surgeon)) and then appropriately energize the actuators attached to the joints to assist in the movement. This will have the distal end moved using powered movement of the joints guided by manual indication of intended direction by the user.

In a further implementation, the spatial position and pose of the distal end or equivalently the mounted external device may be aligned in two stages. The two alignment stages of the present example implementation include 1) gross alignment that may be performed by the user; 2a) fine positioning that may be performed by the user and assisted by the intelligent positioning system; and/or 2b) fine positioning that is performed by the intelligent positioning system independently. The smaller range of motion described in steps 2a) and more apparently in 2b) is optionally bordered by a virtual ring or barrier, such that as the system operates to align the distal end, the distal end does not move at such a pace as to injure the surgeon, patient or anyone assisting the surgery. This is achieved by constraining the motion of the automated arm to within that small ring or barrier. The ring or barrier may represent the extent of the smaller range of motion of the automated arm controlled by the intelligent positioning system.

In further embodiments, the user may override this range and the system may re-center on a new location through step 1 as described above, if the larger range of motion of the automated arm controlled by the intelligent positioning system is also automated.

Figure 9A:
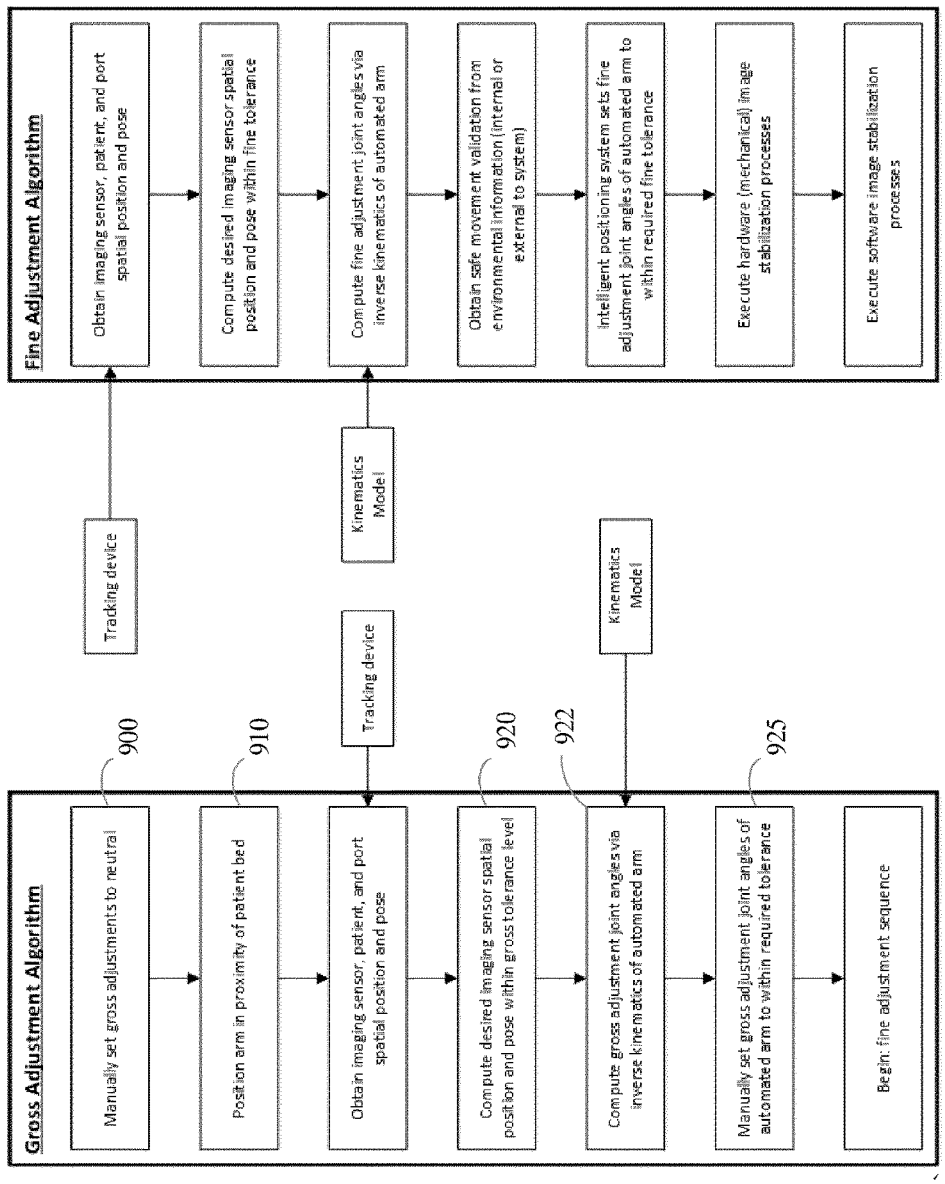
FIG. 9A is a flow chart describing the sequence involved in aligning an automated arm with a target.

An example alignment procedure is illustrated in the flow chart shown in FIG. 9A within the example context of an external imaging device mounted to the automated arm. In this case, a user may initially set the gross alignment joints to a neutral position (900) and wheel it into close proximity of the patient (910). In this position, the intelligent positioning system computes a target end effector spatial position and pose coordinate based on the zero position (920) that will aim the imaging device coaxially (or in another zero position) relative to the access port 100, or, for example, at the tip of a surgical pointer tools 1005 and 1015 shown in FIG. 10B.

In FIG. 9A, the kinematics engine outputs a set of preferred automated arm joint readings to the user that will achieve the zero position within the tolerance achievable by gross alignment (922). The user may then employ these readings to manually perform the initial alignment step (925). In other embodiments, the user may choose to manually adjust the coarse positioning by visual feedback alone, or based on a combination of visual feedback and preferred joint readings. In yet another embodiment, the user may manually perform the initial alignment guided by feedback from the system. For example, the system may provide visual and/or audible information indicating to the user the proximity of the alignment of the system to a pre-selected target range or region of the alignment in the common coordinate frame. The feedback provided may assist the user in identifying a suitable gross alignment, for example, by directing the user's alignment efforts.

In another embodiment, the user may be able to grab the end effector and through a force/torque control loop, guide the end effector into a gross-alignment. This control methodology may also be applied should the surgeon wish to re-orient the external imaging device to be non-coaxial to the access port.

Once the gross alignment is complete, the intelligent positioning system may be employed to perform the fine alignment by moving the automated arm such that the imaging device is brought into the exact zero position via any of the algorithms described above and depicted in FIGS. 8A and 8B. The flow chart shown on the right side of FIG. 9A is another exemplary embodiment describing an automated alignment process which can be executed by the intelligent positioning system again analogous to the flow chart depicted in FIG. 8A.

According to the present embodiments, the alignment of the imaging device is semi-automated; the actions are performed with operator intervention, and feedback from the intelligent positioning system is performed to provide for the fine and/or final alignment of the external device.

During the operator assisted alignment, the spatial position and pose of the imaging device is tracked, for example, by any of the aforementioned tracking methods, such as through image analysis as described above, or by tracking the position of the access port and imaging sensor using reflective markers, also as described above.

The tracked spatial position and pose is employed to provide feedback to the operator during the semi-automated alignment process. A number of example embodiments for providing feedback are presented below. It is to be understood that these embodiments are merely example implementations of feedback methods and that other methods may be employed without departing from the scope of the present embodiment. Furthermore, these and other embodiments may be used in combination or independently.

In one example implementation, haptic feedback may be provided on the automated arm to help manual positioning of the external device for improved alignment. Where an example of haptic feedback is providing a tactile click on the automated arm to indicate the position of optimal alignment. In another example, haptic feedback can be provided via magnetic or motorized breaks that increase movement resistance when the automated arm is near the desired orientation.

In another embodiment, a small range of motion can be driven through, for example magnets or motors, which can drive the spatial position and pose of the external device into desired alignment when it is manually positioned to a point near the optimal position. This enables general manual positioning with automated fine adjustment.

Another example implementation of providing feedback includes providing an audible, tactile or visual signal that changes relative to the distance to optimal positioning of the access port. For example, two audible signals may be provided that are offset in time relative to the distance from optimal position.

As the imaging sensor is moved towards optimal position the signals are perceived to converge. Right at the optimal position a significant perception of convergence is realized. Alternatively, the signal may be periodic in nature, where the frequency of the signal is dependent on the distance from the desired position. It is noted that human auditory acuity is incredibly sensitive and can be used to discriminate very fine changes. See for example: http://phys.org/news/2013-02-human-fourier-uncertainty-principle.html.

Figure 9B:
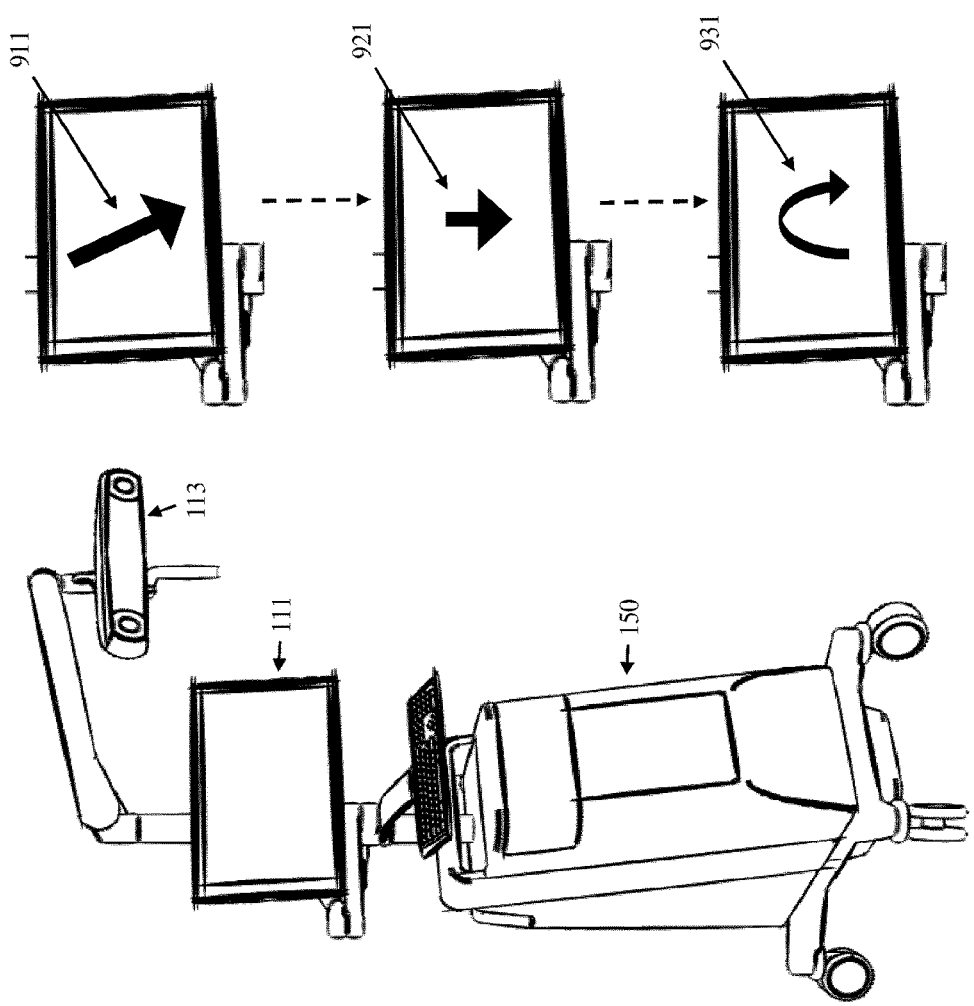
FIG. 9B an illustration depicting a visual cue system for assisting a user in manually aligning an automated arm.

In another example implementation, visual indicators may be provided indicating the direction and amount of movement required to move the imaging sensor into alignment. For example, this can be implemented using light sources such as LEDs positioned on the automated arm, or, for example, a vector indicator on the video display screen of the camera. An example illustration of the vector indicator is shown in FIG. 9B where the arrows 911, 921 and 931 represent visual indicators to the user performing the manual movement. In this figure a shorter arrow 921 represents the spatial position and pose of the imaging device being closer to its required position compared to the longer arrow shown in 911.

Zero Positioning

In an embodiment steps may be taken to set the relative spatial position and pose of the automated arm (mounted with external device or equivalently an imaging device) with respect to the target in the common coordinate frame. for example, that of manually placing the imaging sensor in a chosen spatial position and pose relative to the target spatial position and pose and defining this position to the intelligent positioning system as a zero (chosen) position relative to the port. Which the imaging sensor and accordingly the automated arm should constantly return to, when prompted by the surgeon or automatically by the intelligent positioning system.

Figure 11:
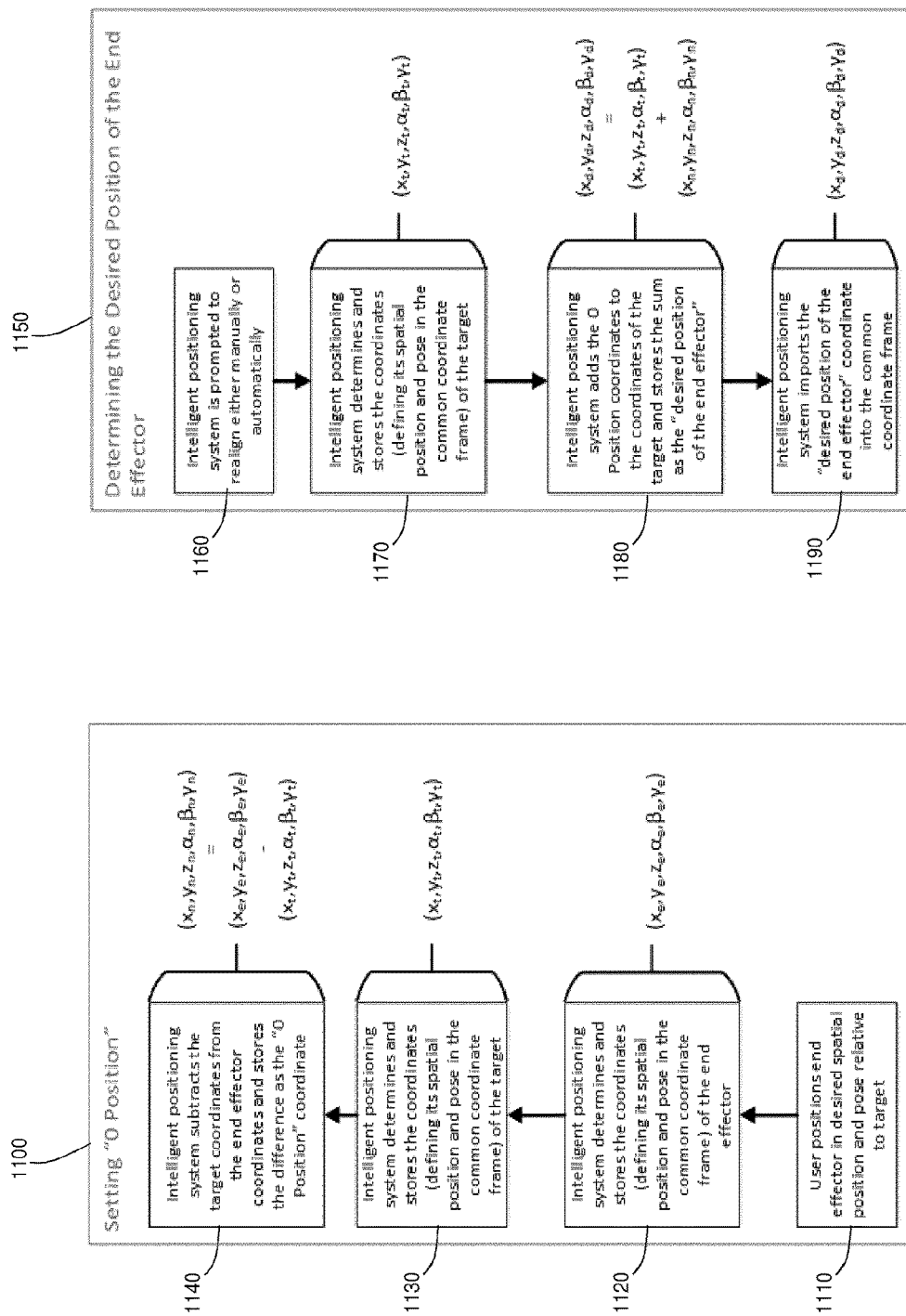
FIG. 11 is a flow chart describing the sequence involved in an embodiment for determining the zero position and desired position of the end effector.

An exemplary embodiment to set the zero position and determine the desired spatial position and pose of the end effector relative to the target are shown in the flow charts in FIG. 11. The left flow chart 1100 describes how to set the zero position and is described further as follows. The first step 1110 is to position the end effector relative to the target in the desired spatial position and pose (manually). Once this is completed the intelligent positioning system moves to the next step 1120 where it acquires the spatial position and pose of the end effector in the common coordinate frame. In the same step it stores this spatial position and pose as coordinates in the common coordinate frame, for example, shown as follows;

$(x_e, y_e, z_e, \alpha_e, \beta_e, \gamma_e)$

Where the subscript "e" denotes the coordinates of the end effector and the variables $\alpha$, $\beta$, and $\gamma$ represent roll, pitch, and yaw respectively. The next step 1130 is the same as the prior step 1120 only that the process is applied to the target. Example coordinates acquired for this step are shown as follows;

$(x_t, y_t, z_t, \alpha_t, \beta_t, \gamma_t)$

Where the subscript "t" denotes the coordinates of the target. The final step 1140 in the flow chart is to subtract the target coordinates from the end effector coordinates to obtain the "Zero Position" coordinates. The "Zero Position" coordinates is a transform that when added to the dynamic target coordinates during surgery can reproduce the relative position of the end effector to the target in the zero position. An example of this calculation is shown as follows;

$$(x_n, y_n, z_n, \alpha_n, \beta_n, \gamma_n)(x_e, y_e, z_e, \alpha_e, \beta_e, \gamma_e) - (x_t, y_t, z_t, \alpha_t, \beta_t, \gamma_t)$$

Where the subscript "n" denotes the "Zero Position" coordinates.

The right most flow chart 1150 in FIG. 11 describes an example of how the intelligent positioning system determines the desired position of the end effector during a surgical procedure and using the "Zero Position" coordinate. The first step 1160 is to prompt the intelligent positioning system to realign the end effector in the zero position. The next step 1170 is to acquire the spatial position and pose of the target in the common coordinate frame. In the same step it stores this spatial position and pose as coordinates, for example shown as follows;

$(x_t, y_t, z_t, \alpha_t, \beta_t, \gamma_t)$

The following step 1180 is to add the "Zero Position" coordinates to the target coordinates to obtain the "desired position of the end effector" coordinates. For example as shown as follows;

$$(x_d, y_d, z_d, \alpha_d, \beta_d, \gamma_d)(x_t, y_t, z_t, \alpha_t, \beta_t, \gamma_t) + (x_n, y_n, z_n, \alpha_n, \beta_n, \gamma_n)$$

Where the subscript "d" denotes the "desired position of the end effector" coordinates. The final step 1190 is to import these coordinates into the common coordinate frame to define to the desired end effector spatial position and pose.

Manual Port Alignment

During an access port procedure, aligning the orientation of the access port for insertion, and ensuring the access port remains in alignment through the cannulation step (as described in more detail below) can be a crucial part of a successful procedure. Current navigation systems provide a display to facilitate this alignment. Some navigation systems are designed to only ensure alignment to the surgical area of interest point regardless of trajectory, while others ensure alignment of a specific trajectory to surgical area of interest point. In any case, this information is displayed on the navigation screen, detached from the view of the actual medical instrument the surgeon is manipulating. With these systems it is often necessary to have a second operator focus on the screen and manually call out distance and orientation information to the surgeon while the surgeon looks at the instrument he is manipulating.

In some embodiments, an alignment device is rigidly and removably connected to the access port, and may also be employed as an alignment mechanism for use during video-based alignment.

Figure 12A:
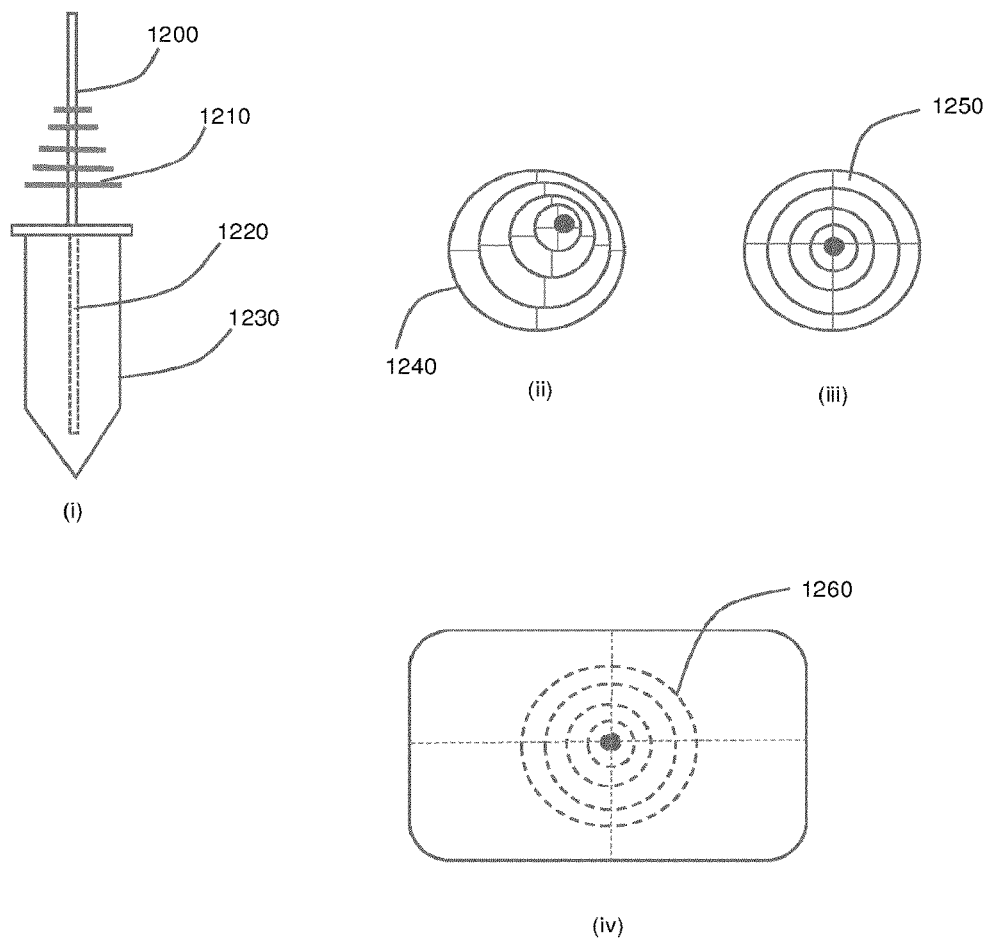
FIGS. 12A-B are exemplary embodiments illustration alignment of an access port in multiple views.
Figure 12B:
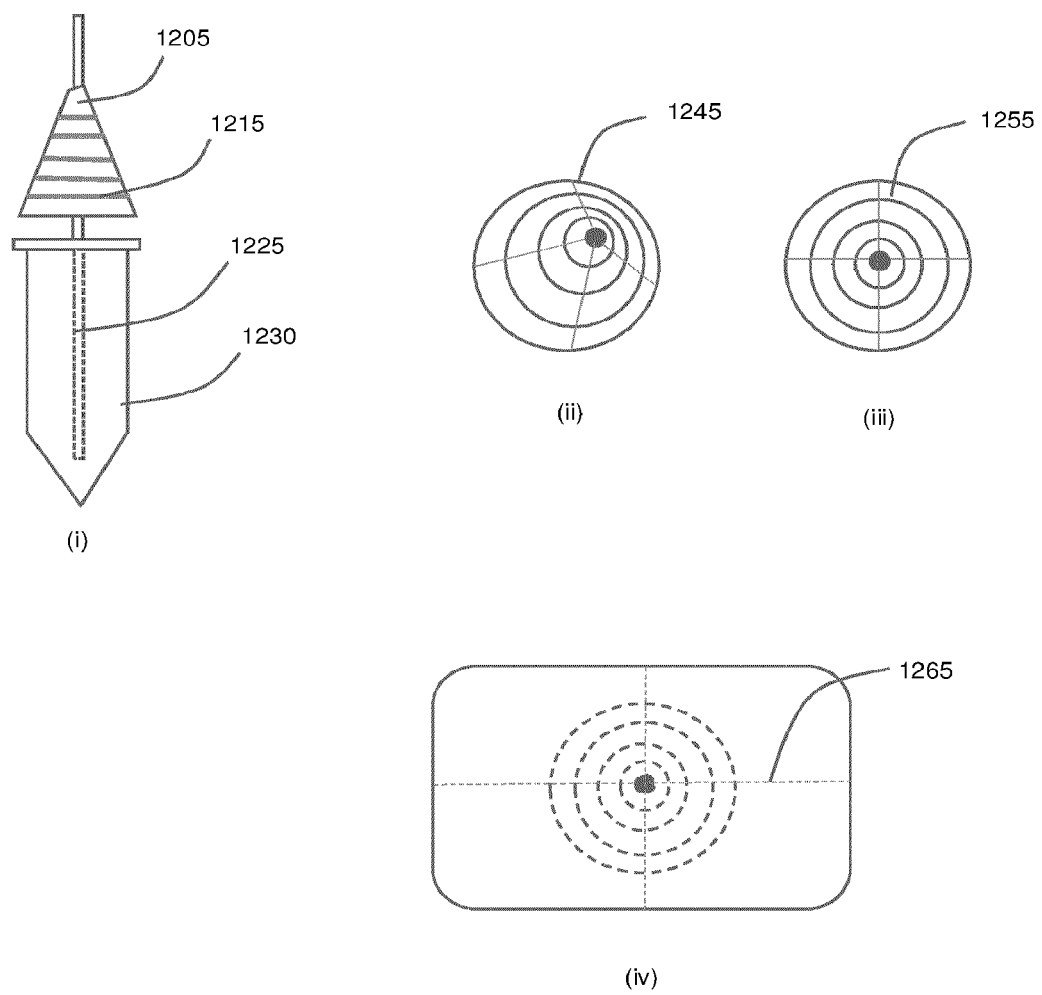

FIG. 12B illustrates an example implementation for aligning an access port based on visual feedback in imaging provided by an external imaging device aligned with the desired trajectory of interest. Conical device 1205 is rigidly and removably attached to access port 1230 with its tip 1225 aligned along the axis of the access port with circular annotations 1215 printed at various depths. When the access port is viewed using an external imaging device with the axis of the external imaging device aligned along the intended insertion path, the circular markers 1215 will appear concentric as shown in FIG. 12B (iii) and (iv). A misaligned access port will result in the circular markers not appearing in concentric fashion. An example of such misalignment is shown in FIG. 12B (ii). Further, a virtual cross-hair 1265 may be displayed on a screen to aid a surgeon to coaxially align the access port while viewing the access port through an externally positioned imaging device. The position of the virtual cross-hair can be based on pre-operative surgical planning and can be the optimal path for inserting the surgical access port for minimizing trauma to the patient.

FIG. 12A illustrates another example implementation in which two or more alignment markers 1210 are provided at different depths along the axis of the access port 1230, optionally with a cross on each alignment marker. These alignment markers can be provided with increasing diameter as the distance increases relative to the imaging device, so that the alignment markers are visible even if partially occluded by nearer alignment markers. In this embodiment, the correct alignment would be indicated by an alignment of all the markers within the annotated representation of the markers, as shown in see FIG. 12A (iii) and (iv).

In one example embodiment, the alignment markers can be provided with a colored edge 1240 that if visible on the imaging device feed, would indicate that the alignment is off axis, as shown in FIG. 12A (ii). The video overlay may also include a display of the depth to the target plane so that the insertion distance can be seen by the surgeon on the same screen as the targeting overlay and the video display of the surgical field.

Modes of Function

In a preferred embodiment the automated arm of the intelligent positioning system will function in various modes as determined but not limited by the surgeon, the system, the phase of surgery, the image acquisition modality being employed, the state of the system, the type of surgery being done (e.g. Port based, open surgery, etc.), the safety system. Further the automated arm may function in a plurality of modes which may include following mode, instrument tracking mode, cannulation mode, optimal viewing mode, actual actuation mode, field of view mode, etc.

The following is a brief summary of some of the modes mentioned above:

Following Mode:

In following mode the automated arm will follow the target at the predetermined (chosen) spatial position and pose as the target is manipulated by the surgeon (for example in the manner illustrated in FIGS. 16C-D and described in detail above), either through electronic or physical means. For the case of the port based surgery commonly used for tumor resection as mentioned above, the surgeon will manipulate the port within the patient's brain as they search for tumor tissue 120 to resect. As the port is manipulated the automated arm mounted with the imaging device will move to consistently provide a constant field of view down the port with lighting conditions geared towards tissue differentiation. This mode can be employed with restrictions to assure that no contact of the arm is made with any other instrument or personnel including the surgeon within the operating room by the process described in the description of FIG. 6C. This restriction can be achieved using proximity sensors to detect obstacles or scene analysis of images acquired for the operating room as described below in greater detail. In addition the surgeon can either dictate the chosen (zero position) spatial position and pose of the arm (including the Imaging device) relative to the target or it can be determined automatically by the system itself through image analysis and navigational information.

Some alternate derivative embodiments of following mode may include

In anti-jitter mode the imaging sensor vibration is compensated for, through the use of various methods such as actuation of magnetic lens, stability coils as well as by slowing the movement of the arm. The jitter can be detected using image analysis software and algorithms as available in the industry today. An example of an anti-jitter mechanism is provided in the [U.S. Pat. No. 6,628,711 B1: Method and apparatus for compensating for jitter in a digital video image]

In delayed following mode the arm is adjusted to assure the predetermined (zero position) spatial position and pose of the imaging device is kept constant, but the following movement has a delay to reduce the probability of minor undeliberate movements of the target (the port 100 in the case of port based surgery)

Instrument Tracking Mode:

In instrument tracking mode the automated arm can adjust the imaging device to follow the medical instruments used by the surgeon, by either centering the focus or field of view and any combination thereof on one instrument, the other instrument, or both instruments. This can be accomplished by uniquely identifying each tool and modelling them using specific tracking marker orientations as described above.

Cannulation Mode:

In cannulation mode the automated arm adjusts the imaging device to an angle which provides an improved view for cannulation of the brain using a port. This would effectively display a view of the depth of the port and introducer as it is inserted into the brain to the surgeon Optimal Viewing Mode:

Given the images captured by the imaging device an optimal viewing mode can be implemented where an optimal distance can be obtained and used to actuate the automated arm into a better viewing angle or lighting angle to provide maximized field of view, resolution, focus, stability of view, etc. as required by the phase of the surgery or surgeon preference. The determination of these angles and distances within limitations would be provided by a control system within the intelligent positioning system. The control system is able to monitor the light delivery and focus on the required area of interest, given the optical view (imaging provided by the imaging sensor) of the surgical site, it can then use this information in combination with the intelligent positioning system to determine how to adjust the scope to provide the optimal viewing spatial position and pose, which would depend on either the surgeon, the phase of surgery, or the control system itself.

Actuation Mode:

Additional modes would be actuation mode in which case the surgeon has control of the actuation of the automated arm to align the imaging device with the target in a chosen spatial position and pose and at a pre-set distance. In this way the surgeon can utilize the target (If a physical object)

as a pointer to align the imaging device in whatever manner they wish (useful for open surgery) to optimize the surgery which they are undertaking.

Field of View Mode:

In field of view mode the automated arm in combination with the imaging device can be made to zoom on a particular area in a field of view of the image displayed on the surgical monitor. The area can be outlined on the display using instruments which would be in the image or through the use of a cursor controlled by a personnel in the operating room or surgeon. Given the surgeon has a means of operating the cursor. Such devices are disclosed in US patents.

Combination of Modes:

The modes mentioned above and additional modes can be chosen or executed by the surgeon or the system or any combination thereof, for example the instrument tracking mode and optimal lighting mode can be actuated when the surgeon begins to use a particular tool as noted by the system. In addition the lighting and tracking properties of the modes can be adjusted and made to be customized to either each tool in use or the phase of the surgery or any combination thereof. The modes can also be employed individually or in any combination thereof for example the Raman mode in addition to the optical view mode. All of the above modes can be optionally executed with customized safety systems to assure minimization of failures during the intra-operative procedure.

Optimization of View at End of Port

In the context of an imaging device formed as a camera imaging device with a configurable illumination source, supported by the automated arm, alignment with the access port may be important for a number of reasons, such as, the ability to provide uniform light delivery and reception of the signal. In addition, auto-focus of the camera to a known location at the end of the access port may be required or beneficial.

In some implementations, the present embodiments may provide for accurate alignment, light delivery, regional image enhancement and focus for external imaging devices while maintaining an accurate position. Automated alignment and movement may be performed in coordination with tracking of the target (access port). As noted above, this may be accomplished by determining the spatial position and/or pose of the target (access port) by a tracking method as described above, and employing feedback from the tracked spatial position and/or pose of the external imaging device when controlling the relative position and/or pose of the external imaging device using the automated arm.

In an embodiment, directional illumination device such as a laser pointer or collimated light source (or an illumination source associated with an imaging device supported by the automated arm) may be used to project.

Optical Optimization of Port

In yet a further embodiment, a calibration pattern is located at or near the proximal end of the access port. This pattern will allow the camera imaging device to automatically focus, align the orientation of its lens assembly, and optionally balance lighting as well as color according to stored values and individual settings. An exemplary method used to identify the particular type of port being used is the template matching method described above. The template 1030 shown in FIG. 10A, can be used to provide the required information about the port dimensions for optimal lighting and focus parameters that the imaging device can be configured to conform with.

Another stage of alignment may involve the camera imaging device focusing on the tissue deep within the access port, which is positioned at a known depth (given the length of the access port is known and the distance of the port based on the template on the proximal end of the port). The location of the distal end of the access port 100 will be at a known position relative to the imaging sensor 104 of FIG. 1 and tracked access port 100, in absolute terms, with some small-expected deviation of the surface of the tissue bowing into the access port at the distal end. With a given field of view, camera optical zoom/focus factors, and a known distance from the detector to end of access port, the focus setting can be predetermined in a dynamic manner to enable auto-focus to the end of the tissue based simply on tracking of the access port and camera location, while using some known settings (camera, access port length, focus optics/mechanics, desired field of view). In this manner, a stable focus can be established to maximize the desired field of view.

In a similar, closed-loop manner, color and white balance of the imaging device output can be determined through suitable imaging processing methods. A significant issue with current surgical optics is glare caused by fluids reflecting the intense illumination in the surgical cavity. The glare causes imbalance in the dynamic range of the camera, where the upper range of the detectors dynamic range is saturated. In addition, the illumination intensity across the frequency spectrum can be unbalanced depending on the illumination and surgical conditions. By using a combination of calibration features or targets on the access port (100), and using pre-set parameters associated with the combination of camera and light source, the images can be analyzed to automatically optimize the color balance, white balance, dynamic range and illumination uniformity (spatial uniformity). Several published algorithms may be employed to automatically adjust these image characteristics. For example, the algorithm published by Jun-yan Huo et. al. ("Robust automatic white balance algorithm using gray color points in images," IEEE Transactions on Consumer Electronics, Vol. 52, No. 2, May 2006) may be employed to achieve automatic white balance of the captured video data. In addition, the surgical context can be used to adapt the optimal imaging conditions. This will be discussed in greater detail below.

Two Stage Method Image Optimization

Alternatively, in a two-step approach, the tracking system can be employed, in a first step of alignment, to track the position of the access port, for a gross calculation of spatial position and pose. This allows for an imaging device 104, as seen in FIG. 1, to be positioned in a co-axial manner relative to the port 100, and at the appropriate focal distance and focal setting based on the field of view, resolution, and frame rate, defined by the user. This will only be accurate within the tolerance of the tracking capability of the system, the mechanical positioning accuracy of the automated arm, and the tissue deflection at the tip of the access port.

A second stage alignment, based on imaging optimization and focus, can optionally be achieved by interaction of the imaging sensor, positioning of the automated arm, analysis of the images, and the use of range detection to the end of the access port (for example by template matching), and centered at the distal end of the access port. For example, as is currently done with more traditional auto-focus functions of digital camera systems, the image can be analyzed to determine the sharpness of the image by way of image metric quantification in a series of focal zones. The focal zones would be directed to a location at the end of the access port, where the gross positioning of the system would allow for this fine, and more focused approach to automatically detect the focal zone as being within the field of view of the end of the access port. More specifically, this is defined as a zone smaller than the field of view of the access port.

In addition, one or more range detectors can be used, optionally through the lens of the imaging device 104, so that the actual position of the tissue at the end of the access port can be calculated. This information can be provided as input into the iterative algorithm that determines the optimal imaging device position, and focal settings.

Optimized Illumination and Data

The coaxial alignment of the imaging sensor with the access port, enables efficient light delivery to the end of the access port which is vital to acquiring higher resolution imaging, as well as the ability to focus optics so as to enhance or maximize the detector efficiency. For instance, with a poorly aligned access port and imaging sensor, only a small fraction of the imaging sensor is utilized for imaging of the area of interest, i.e. the end of the access port. Often only 20% of the total detector is used, while a properly aligned imaging sensor can yield 60%+ detector efficiency. An improvement from 20% to 60% detector efficiency roughly yields an improved resolution of 3 times. A setting can be established on the system to define a desired efficiency at all times. To achieve this, the intelligent positioning system will actuate the movement of the automated arm, mounted with the imaging sensor, and focus it at the distal end of the access port as it is maneuvered by the surgeon to achieve the desired detector efficiency, or field of view.

Homgenized Light Delivery

Figure 13:
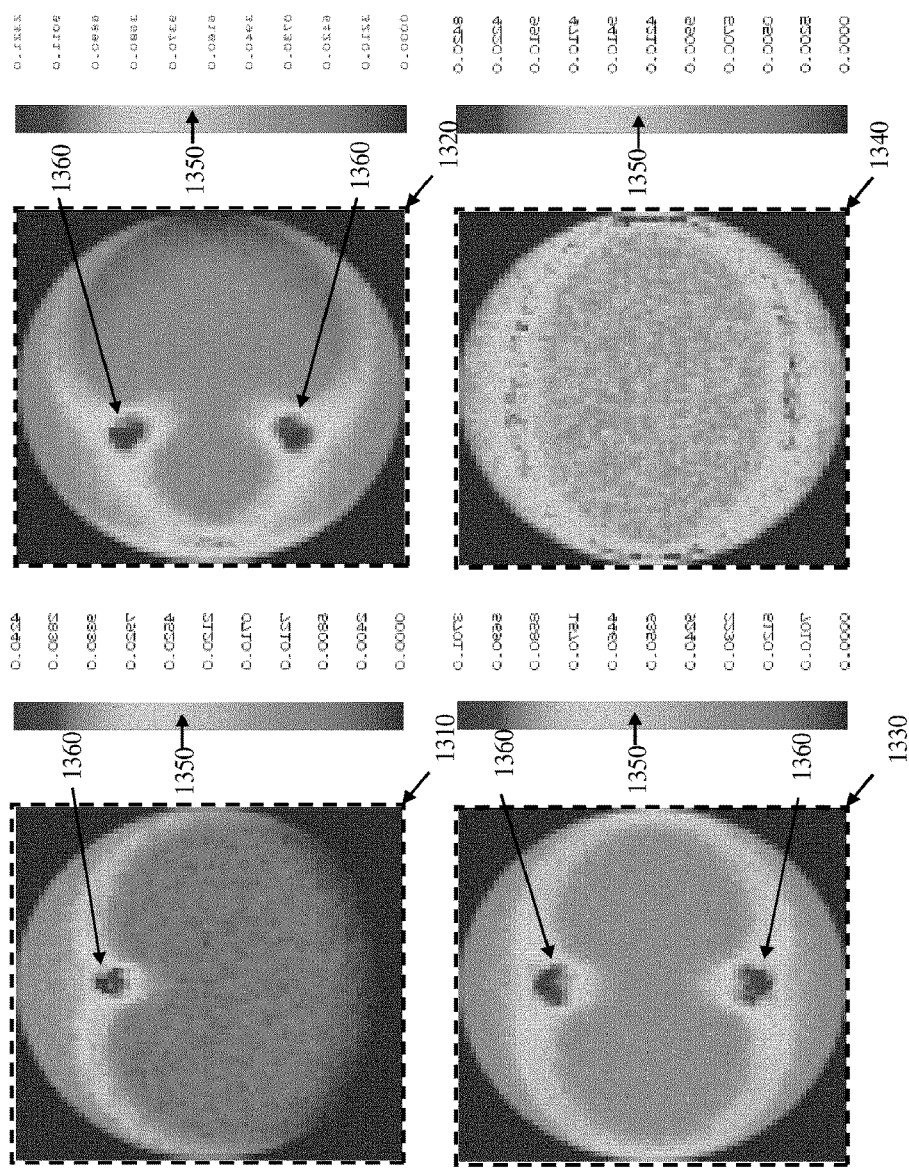
FIG. 13 an illustration depicting port characteristics that can be utilized in optical detection methods.

Another advantageous result of this embodiment is the delivery of homogenized light through the port to the surgical area of interest permitting improved tissue differentiation between healthy and unhealthy brain tissue by potentially reducing glare and reducing shadows which fall on the tissue due to the port. For example the intelligent positioning system can utilize light ray tracing software (such as ZMAX) to model the system given the constraints of the spatial position, pose and 3D virtual model of the port as well as the spatial position, pose and model illumination source as shown in FIG. 13. The first model 1310 shows the illumination of the region of interest using a single illumination element on the external imaging device at a given distance and pose relative to the port. The second 1320 and third 1330 models show illumination of the region of interest using illumination from two sources each. The pairs of sources in each model are oriented differently with respect to the other model. Both models two and three have the same distance and pose parameters as model one relative to the port. The final model 1340 shows illumination from two sources with the same orientation as the sources in the second model 1320 relative to the imaging device, with the same pose but, a different distance. The color map on each region of interest (distal end of the port) shown in the figure describes the illumination level, where mid-range 1350 represents the ideal illumination level.

As can be seen in FIG. 13, hot spots 1360 exist in models one through three (1310, 1320, 1330) which result in heavy glare at those positions and inadequate imaging for the surgeon, while model four 1340 provides the optimal lighting condition (homogenized and low glare delivery of illumination). Using model four as the optimal spatial position and pose alignment of the illumination source, the automated arm would position the imaging sensor (inclusive of the illumination source) to achieve this particular illumination level map thereby improving the view of the surgical area of interest for the surgeon. The software can then determine the optimal spatial position and pose of the illumination source (the Imaging device in this case) relative to the target (port) given the restrictions of the system (minimum offset 575 as shown in FIG. 6A-B) to ensure optimal light delivery through the port to the region of interest. The illumination source may be also optimally positioned after modelling the shadow cast by the surgical tools. In other words, the target region within the field of view may be optimally illuminated while avoiding casting of shadows from the medical instruments utilized by the surgeon within the port. This is possible given the spatial position and pose of the medical instrument can be estimated using tracking markers placed on the surgical tools.

Figure 14A:
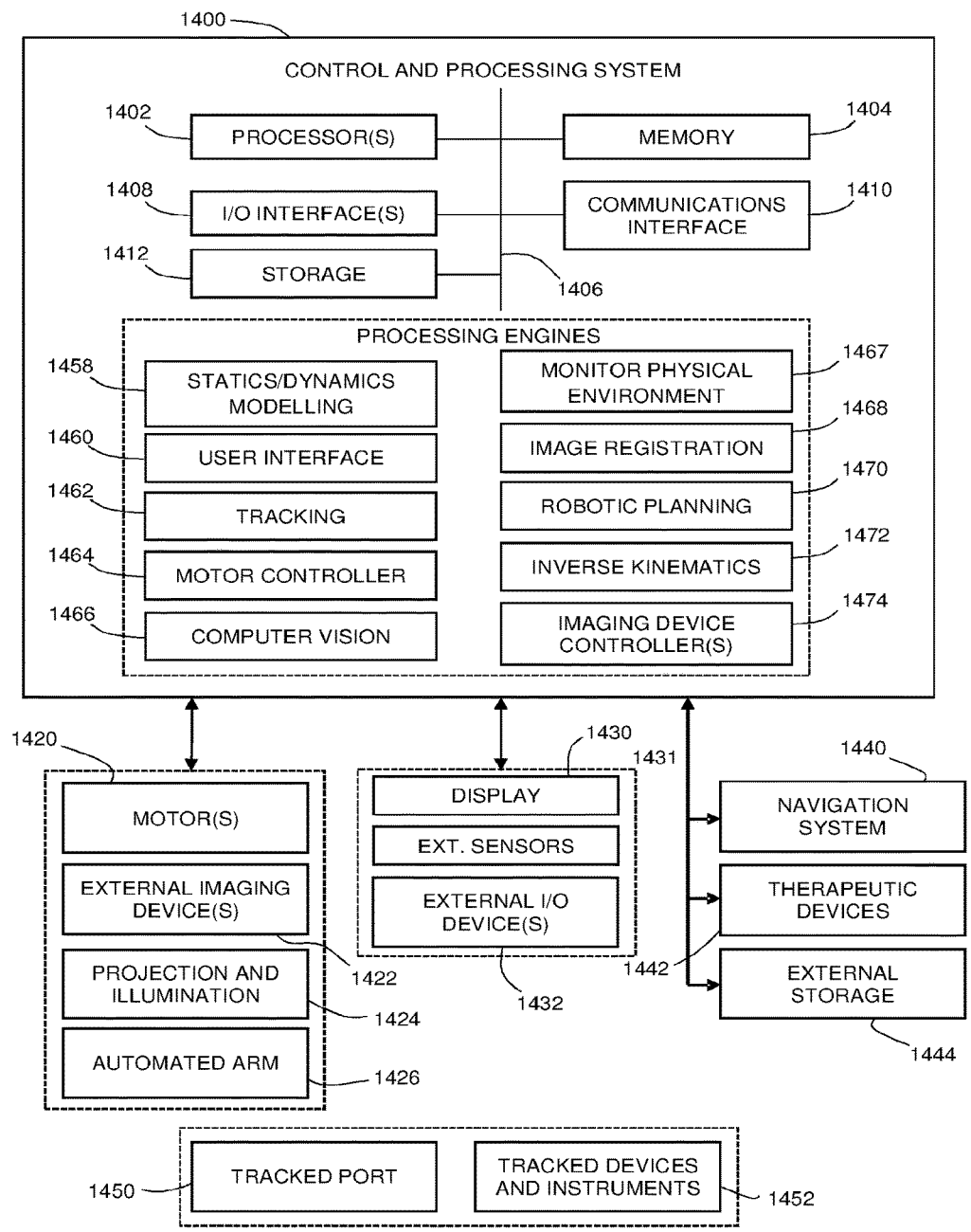
FIGS. 14A-B are block diagrams showing an exemplary navigation system including an intelligent positioning system.
Figure 14B:
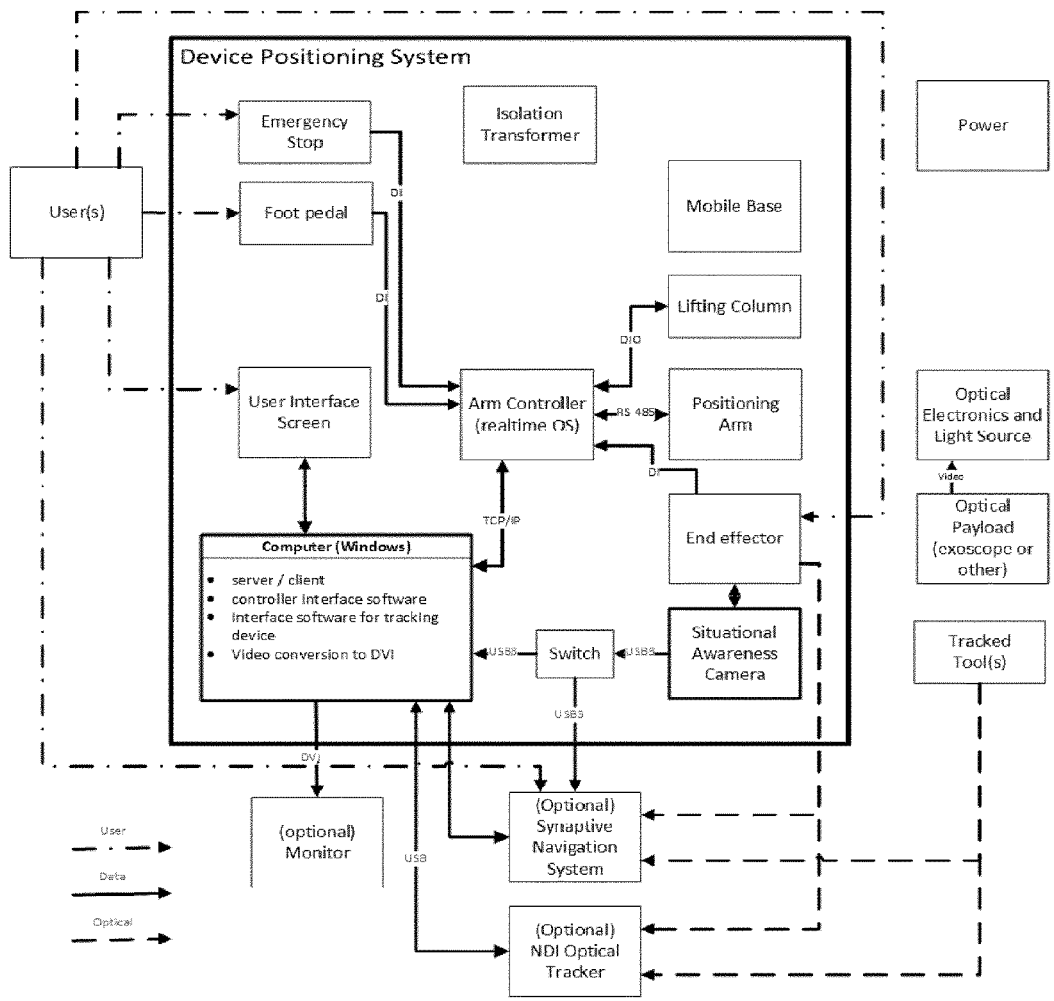

Referring now to FIGS. 14A and 14B, a block diagram of an example system configuration is shown. The example system includes control and processing system 1400 and a number of external components, shown below.

As shown in FIG. 14A, in one embodiment, control processing system 1400 may include one or more processors 1402, a memory 1404, a system bus 1406, one or more input/output interfaces 408, a communications interface 1410, and storage device 1412. Processing and control system 1400 is interfaced with a number of external devices and components, including, for example, those associated with access port imaging and tracking, namely motor(s) 1420, external imaging device(s) 1422, projection and illumination device(s) 1424, and automated arm 1426. External user input and user interface rendering is facilitated by one or more displays 1430 and one or more external input/output devices 1426 (such as, for example, a keyboard, mouse, foot pedal, microphone and speaker).

Processing and control system 1400 is also interfaced with an intelligent positioning system 1440 inclusive of a tracking device 113 for tracking items such as an access port 100 in FIG. 4E or 1450 in FIG. 14 and one or more devices or instruments 1452. Additional optional components include one or more therapeutic devices 1442 that may be controlled by processing and control system 1400, and external storage 1444, which may be employed, for example, for storing pre-operative image data, surgical plans, and other information.

It is to be understood that the system is not intended to be limited to the components shown in FIG. 1400. One or more components control and processing 1400 may be provided as an external component that is interfaced to a processing device. In one alternative embodiment, navigation system 1440 may be integrated directly with control and processing system 1400.

Embodiments of the disclosure can be implemented via processor 1402 and/or memory 1404. For example, the functionalities described herein can be partially implemented via hardware logic in processor 1402 and partially using the instructions stored in memory 1404, as one or more processing engines. Example processing engines include, but are not limited to, statics and dynamics modeling engine 1458, user interface engine 1460, tracking engine 1462, motor controller 1464, computer vision engine 1466, engine to monitor surrounding environment of the automated arm based on sensor inputs 1431, image registration engine 1468, robotic planning engine 1470, inverse kinematic engine 1472, and imaging device controllers 1474. These example processing engines are described in further detail below.

Some embodiments may be implemented using processor 1402 without additional instructions stored in memory 1404. Some embodiments may be implemented using the instructions stored in memory 1404 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, non-volatile memory and/or cache. Portions of this software and/or data may be stored in any one of these storage devices.

It is further noted that in some embodiments, unlike a typical automated arm which has to account for unknown weight of the material picked up by the distal end, automated arm need only account for the known weight of external devices (such as imaging devices) attached to the distal end. Hence, known statics and dynamics of the entire automated arm can be modeled a priori (e.g. via engine 1458 of FIG. 14) and this knowledge can be incorporated in the accurate control of the arm during tracking. Further, imaging and tracking modalities can be used to provide situational awareness for the automated arm, as described above. This situational knowledge can be incorporated during tracking of the access port by the external device or devise supported by the arm to avoid accidental collision of the arm with obstacles in the path such as surgical team, other equipment in the operating room and the patient. This situational awareness may also arrive from proximity sensors optionally mounted on the automated arm and/or distal end, as noted above.

In one embodiment the system is configured consistently with the block diagram shown in FIG. 14B. FIG. 14B is an exemplary embodiment of the intelligent positioning system illustration utilized in connection with a navigation system. The descriptions below outline various exemplary communication paths which may be utilized throughout the intelligent positioning system (IPS).

User→Foot Pedals→Arm Controller→Positioning Arm

The surgeon has three discrete-input pedals to control the IPS:
1. Align to Tool: Pressing this pedal 155 shown in FIG. 1 will align the scope 266 to the target (such as the port 100) that is currently being tracked. The pedal 155 needs to be continuously held during the motion to the point of the tool at the time the pedal was initially depressed. The user needs to press the pedal again to realign.
2. Increase Standoff: The pedal will increase the standoff distance 675 between the selected tool and the scope. The distal end will move at constant velocity while depressed. The standoff distance can be increased until reach limits of the automated arm are obtained.
3. Decrease Standoff: This pedal decreases the standoff distance 675, at a constant velocity, of the distal end and the selected tool. This motion will cease once a minimum standoff distance is reached (dependent upon scope and tool selected).

These pedals are connected to the digital inputs on the automated arm through the intelligent positioning system 250. The automated arm controller sends joint-level commands to the motor drivers in the automated arm.

These foot-pedals may be enhanced to include Optics control as well.

User→Touch Screen→UI Computer→Arm Controller

The user can interface with the robot through a touch screen monitor. These are generally done prior to surgery.
1. Initialize the joints: As the robot arm only has relative encoders, each joint must be moved up to 20 degrees for the system to determine its absolute position. The UI provides an initialization screen in which the user moves each joint until the encoders are initialized.
2. Selection of imaging sensor: Selection of imaging sensor on the UI computer gets sent to the automated arm controller. The different imaging sensors have different masses, and different desired relative spatial positions and poses relative to the target (for example the port).
3. Selection of tracked medical instrument: Selection of which target to track (given multiple targets, for example a port or a medical instrument or etc.) on the UI computer gets sent to the automated arm controller.
4. Degree of Freedom Selection: The user can select if the tool will be tracked in 6-, 5- or 3-DoF mode.
5. Set 0 position: Set a new spatial position and pose of the automated arm (and consequently the imaging sensor given it is mounted on the automated arm) with respect to a target (for example the port)

NDI Optical Tracker→UI Computer→Arm Controller

The NDI tracking system acquires the distal end (or equivalently the imaging sensor) spatial position and pose within its field of view. It sends this data to the UI Computer which shares the tracked target and distal end information with the automated arm controller so that the spatial position and pose can be calculated. It may also use the patient reference and registration to determine a no-access zone.

Situational Awareness Camera→UI Computer→Monitor

The situational awareness camera (specific embodiment of an imaging sensor) provides imaging of the surgical site. This imaging is sent to the UI computer which turns them into a video stream which is output to an external monitor. As well, the UI computer may overlay warnings, error messages or other information for the user on the video stream.

Phases of Port Based Surgery

Figure 15:
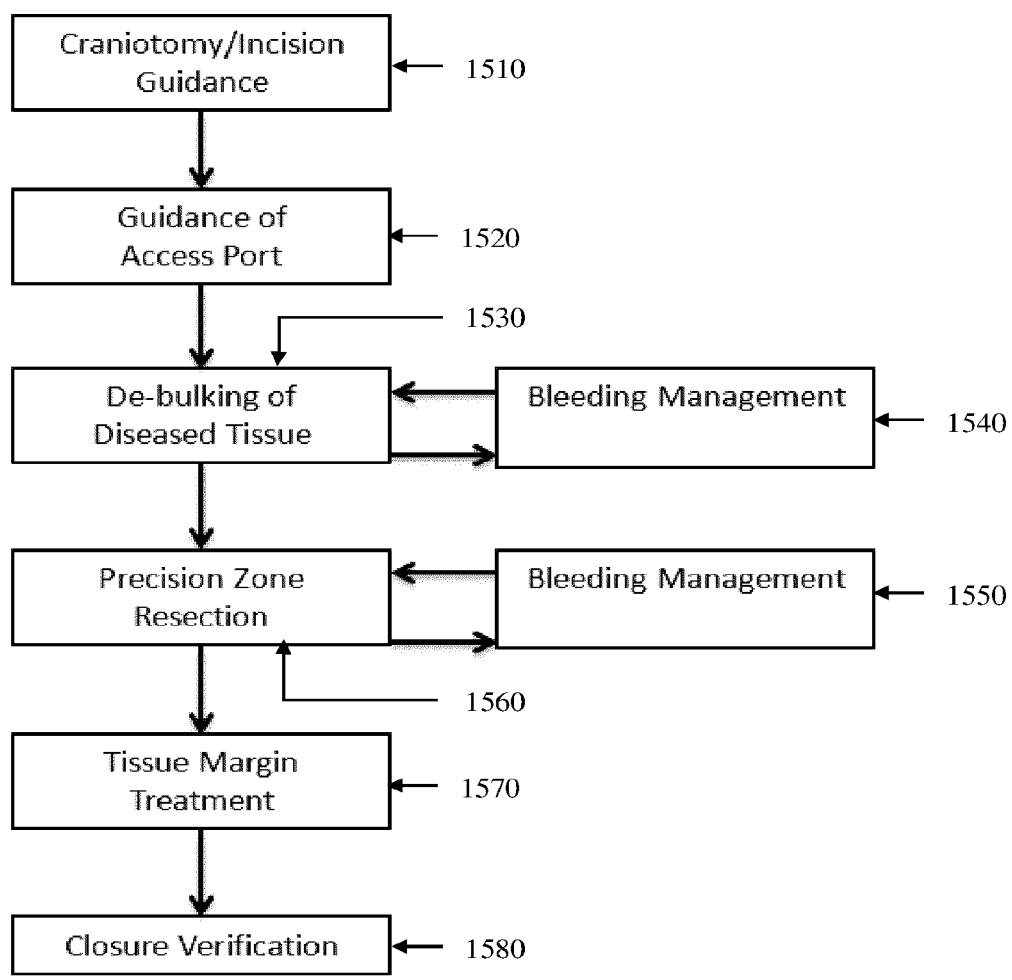
FIG. 15 is a flow chart describing the steps of a port based surgical procedure.

An example phase breakdown of the port based surgical operation is shown in FIG. 15. The arm can be utilized in a corresponding manner to each of the phases to compliment and ease the surgeons process during each step.

The first step (1510) is the incision of the scalp and craniotomy. During these procedures the automated arm (102) (connected to the imaging device (104)) can be implemented to guide the surgeon to the correct position of the craniotomy with respect to the brain within the skull automatically. This is achievable through the use of the navigation system conjointly with the automated arm.

Once the incision and craniotomy are completed the surgery enters the next phase (1520) and the automated arm can be used to perform an US above the dura either automatically by the system or manually by the surgical team. Using this information and input from the intelligent positioning system the automated arm (with mounted imaging device) can project the sulci onto the dura to allow for a better guidance of the dura incision and increased orientation awareness. After the dura incision the cannulation process begins. In this subphase the automated arm can be adjusted to an alternate angle to provide a view of the graduation marks on the port whilst its being cannulated into the brain so the surgeon can see its depth.

In the next simultaneous phases (1530 and 1540) the automated automated arm 102 has the most utility as it aids in providing clear images of the distal end of the port for gross de-bulking of unhealthy brain tissue. During this step the surgeon 201 will maneuver the port 100 in the brain of the patient 202 through a multiplicity of motions (for example 1665 in FIG. 16C) to resect the tumor (120), as the distal end of the port in most cases does not provide the access needed to resect the entire tumor in one position an example of this is shown in FIG. 16C as the unaccessible part of the tumor 1680. As the port is maneuvered the automated arm (with connected imaging device) can follow the port in a coaxial manner to consistently provide a view of the distal end (for example as shown in FIG. 6A-B) where the surgeons tools (for example (1612)) are operating, an example flow of the constant alignment of the automated arm and connected scope is provided in FIG. 8B. This saves the surgeon and surgical team time and streamlines the surgical process by preventing the surgical team from having to constantly readjust the imaging device to view down the port at the correct angle to provide the required surgical view as is required in present surgical systems such as the UniArm Surgical Support System (by Mitaka USA Inc.). This also increases the accuracy of the surgeon by keeping the display of the surgical site in the same direction (relative to brain anatomy or any other reference) resulting in the surgeon remaining directionally oriented with the surgical site of operation. Another way the automated arm (as part of the intelligent positioning system) increases accuracy is by removing the need for the surgeon to reorient himself with the space (inside the brain) when working as a result of removing their instruments and readjusting the imaging sensor which is combined manually to an adjustable arm. In addition the automated arm can also align the illumination device (connected to either the distal end, or the imaging sensor) in orientations to provide ideal lighting to the distal end of the port. In this phase the automated arm can also perform other alignment sequences required for other imaging modalities for example, stereoscopic imaging as described above for 3D imaging. The automated attainment of stereoscopic images can readily provide more information to the surgeon again increasing their accuracy during the procedure. The automated arm 102 can also provide other imaging modalities through the use of imaging probes by automated insertion into the port or automated external scanning as required by the surgeon or determined by the navigation system in combination with the intelligent positioning system.

After the bulk resection phase the surgical procedure enters the next two simultaneous phases of fine-resection (1550 and 1560). In this phase the surgeon removes the tumor from the fringes of healthy tissue, by differentiating, using their knowledge, between the healthy and unhealthy tissue. During fine-resection the automated arm is used in a similar manner to the gross debulking phase above.

The next phase of surgery (1570) could potentially require the automated arm to deliver therapeutic agents to the surgical site to remove any remaining unhealthy tissue from the area and assure an optimal recovery. This step can be accomplished by the navigation system in combination with the intelligent positioning system and its maneuvering of the automated arm down the port to the correct site where a therapeutic distal end instrument could be used to supply the therapeutics. In addition the arm could possibly be provided the ability to maneuver the port as required to achieve effective delivery to all sites automatically based on inputs provided by the navigation system and/or the surgeon.

The final step (1580) involves the removal of the port and closure of the wound in addition to the application of materials to assist in healing the surgical area. In this step the automated arm is used in a similar manner to the gross de-bulking step in that the automated maneuvering of the arm by the system follows the surgeons surgical tool to provide the required view. Once the port is removed the automated arm is maneuvered in a similar manner to the incision step providing the correct view of the surgical area during the suturing of the wound.

In another embodiment the intelligent positioning system can be provided with presurgical information to improve arm function. Examples of such information are a system plan indicating the types of movements and adjustments required for each stage of surgery as well as the operating theater instruments and personnel positioning during the phases of surgery. This would streamline the surgical process by reducing the amount of manual and customized adjustments dictated by the surgeon throughout the procedure. Other information such as the unique weights of the imaging sensors can be inputted to assure a smooth movement of the arm by automatic adjustment of the motors used to run it.

Singularities

The American National Standard for Industrial Robots and Robot Systems—Safety Requirements (ANSI/RIA R15.06-1999) defines a singularity as "a condition caused by the collinear alignment of two or more robot axes resulting in unpredictable robot motion and velocities." It is most common in robot arms that utilize a "triple-roll wrist". This is a wrist about which the three axes of the wrist, controlling yaw, pitch, and roll, all pass through a common point. An example of a wrist singularity is when the path through which the robot is traveling causes the first and third axes of the robot's wrist (i.e. robot's axes 4 and 6) to line up. The second wrist axis then attempts to spin 3600 in zero time to maintain the orientation of the end effector. Another common term for this singularity is a "wrist flip". The result of a singularity can be quite dramatic and can have adverse effects on the robot arm, the end effector, and the process. Some industrial robot manufacturers have attempted to side-step the situation by slightly altering the robot's path to prevent this condition. Another method is to slow the robot's travel speed, thus reducing the speed required for the wrist to make the transition. The ANSI/RIA has mandated that robot manufacturers shall make the user aware of singularities if they occur while the system is being manually manipulated.

A second type of singularity in wrist-partitioned vertically articulated six-axis robots occurs when the wrist center lies on a cylinder that is centered about axis 1 and with radius equal to the distance between axes 1 and 4. This is called a shoulder singularity. Some robot manufacturers also mention alignment singularities, where axes 1 and 6 become coincident. This is simply a sub-case of shoulder singularities. When the robot passes close to a shoulder singularity, joint 1 spins very fast.

The third and last type of singularity in wrist-partitioned vertically articulated six-axis robots occurs when the wrist's center lies in the same plane as axes 2 and 3.

Self-Collision and Singularity Motion Interlock

Having the automated arm be mobile instills another constraint on the intelligent positioning system, which is to ensure the mobile base and the automated arm are not simultaneously in motion at any given time. This is accomplished by the system by having an auto-locking mechanism which applies brakes to the arm if the wheel brakes for the mobile base are not engaged. The reasoning for this constraint is movement of the arm without a static base will result in motion of the base (basic physics). If the arm is mounted on a vertical lifting column, the lifting column adds to this constraint set: the lifting column cannot be activated if the mobile base wheels are not braked or if the arm is in motion. Similarly, the arm cannot be moved if the lifting column is active. If the mobile base wheel brakes are released, the arm and lifting column are both disabled and placed in a braked state.

Additional Mode Constraints

Consider adding—it only moves in regard to a parameter based on
- the image—for example if the percentage of the image from the bottom of the port is least a certain percentage of the total image—or some relevant parameter
- the axial alignment—for example it moves if it is off co-axial by certain degrees greater than x Accordingly, in some embodiments of the present disclosure, system, devices and methods are described that employ imaging devices, guidance devices, tracking devices, navigation systems, software systems and surgical tools to enable a fully integrated and minimally invasive surgical approach to performing neurological and other procedures, such as previously inoperable brain tumors, in addition to the intracranial procedure using the port based method described above. It is to be understood, however, that the application of the embodiments provided herein is not intended to be limited to neurological procedures, and may be extended to other medical procedures where it is desired to access tissue in a minimally invasive manner, without departing from the scope of the present disclosure. Non-limiting examples of other minimally invasive procedures include colon procedures, spinal, orthopedic, open, and all single-port laparoscopic surgery that require navigation of surgical tools in narrow cavities. The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Figure 17:
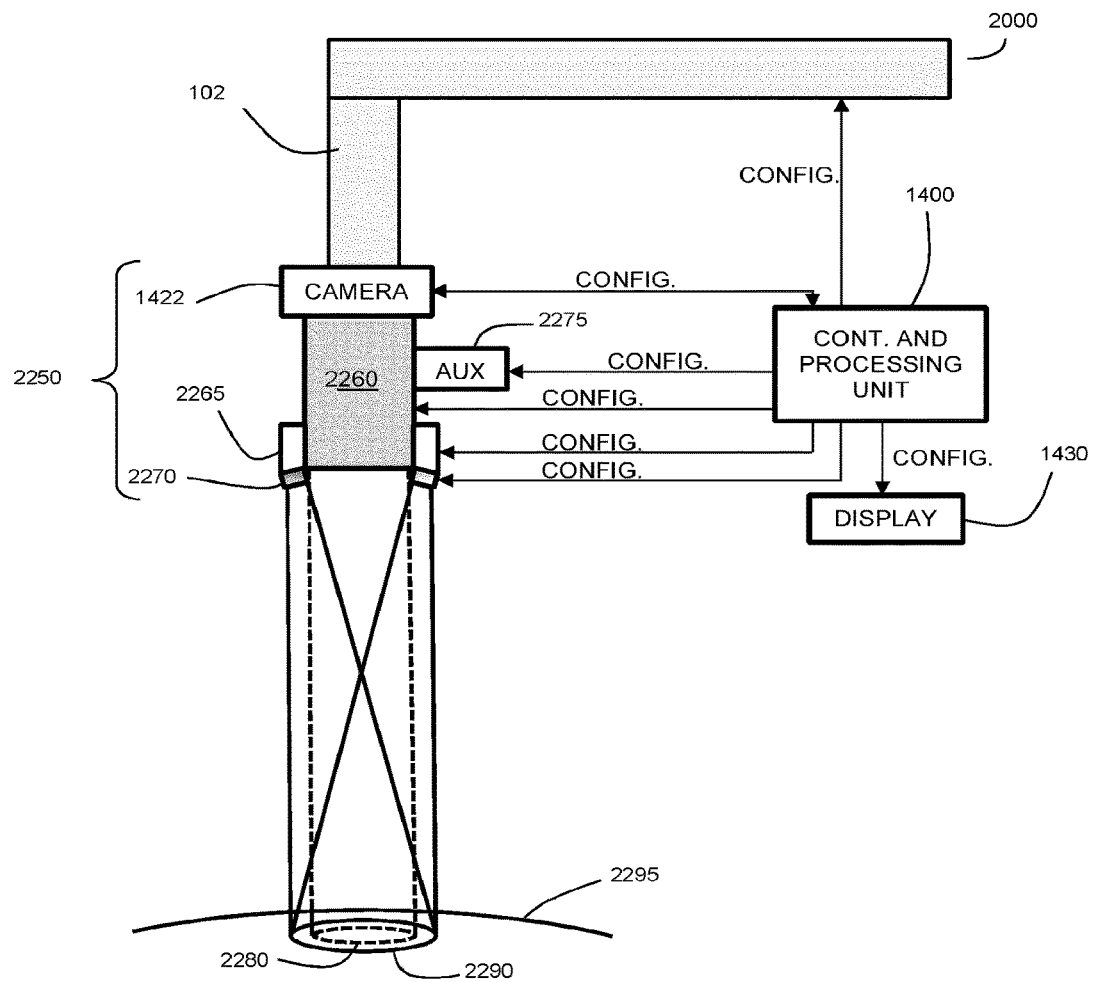
FIG. 17 illustrates an example surgical system including an optical imaging system and associated control system such as may be used for an autofocus system.

Referring to FIG. 17, an example surgical system 2000 is shown including an optical imaging system and associated control system such as may be used for an autofocus system. Control and processing unit 1400 may be interfaced with one or more components of optical system 2250 in order to dynamically provide configuration parameters based on the intraoperative identification of one or more medical instruments. Control and processing unit 1400 is shown interfaced with camera 1422, imaging optics assembly 2260, illuminators 2265, illumination focusing optics 2270, and auxiliary imaging modality assembly 2275. Upon detection of a medical instrument, the configuration data may be accessed in order to determine customized configuration parameters for one or more components of the optical system, and the customized configuration parameters may be employed to configure or reconfigure the one or more components.

In the example case illustrated in FIG. 17, a coarse resection tool (not shown in the figure) has been identified. Customized configuration parameters are obtained for customizing one or more of camera 1422, imaging optics assembly 2260, illuminators 2265, illumination focusing optics 2270, auxiliary imaging modality assembly 2275, robotic arm 102, and a user interface displayed on display 1430, based on the identification of the coarse resection tool. When the coarse resection tool is removed from the surgical field and a fine resection tool is brought within the surgical field, the absence of the gross section tool and the presence of the fine resection tool is detected, with the fine resection tool being identified by the system as described above. New customized configuration parameters are obtained, and the optical system 2250 is reconfigured. In this example, configuration parameters for a number of components have been modified due to the identification of the fine resection device. Specifically, robotic arm 105 has been repositioned according to updated configuration parameters to achieve a reduced working distance; imaging optics assembly has been reconfigured to provide a reduced field of view 2280 and therefore higher magnification; illumination focusing optics 2270 have been reconfigured to produce a reduced illumination region; and illuminators 2265 have been reduced in intensity in order to preserve the intensity of illumination within the illumination region 2290. Additionally, for example, the system may be further reconfigured by providing configuration parameters for any one of more of room lights (e.g. dimming or increasing brightness), coarse resection tool reconfiguration, fine resection tool reconfiguration, adjustment of speed and/or power of the fine resection tool, modifying hanging protocols displayed on the navigation screen (e.g. display different sets of images and different views of those images), and adjust the angle or height of the surgical table.

In one embodiment, fine resection tool is tracked by the tracking system, and the customized configuration parameters configure robotic arm 102 to be actuated such that the field of view 2280 of imaging optics assembly 2260 is actively translated to overlap with the distal tip of the fine resection device based on closed-loop feedback from the tracking system. In one example implementation, control and processing unit 1400 may be interfaced with camera 1422 in order to adaptively provide configuration parameters associated with one or more of, but not limited to, imaging frame rate, gain, saturation, shutter speed, ISO, aperture size, on-chip binning, image size, digital zoom (ROI), and cooling temperature (e.g. if thermo-electric cooling is available).

Control and processing unit 1400 may additionally or alternatively be interfaced with imaging optics assembly 2260 in order to provide configuration parameters associated with one or more of, but not limited to, zoom (magnification), focal length, working distance, numerical aperture, polarization sensitivity, attenuation, filter wavelength, depth of field, image stabilization and field of view. For example, imaging optics assembly 2260 may include one or more actuators for varying these settings according to the configuration parameters that are provided. Control and processing unit 1400 may additionally or alternatively be interfaced with illuminators 2265 in order to provide configuration parameters associated with one or more of, but not limited to, illumination intensity, illumination wavelength, illumination angle, pulsed or continuous operation, and number of active illuminators. For example, illuminators 2265 may include one or more actuators for varying the incidence angle of the illumination beams according to the configuration parameters that are provided. Control and processing unit 1400 may additionally or alternatively be interfaced with illumination focusing optics 2270 in order to provide configuration parameters associated with one or more of, but not limited to, focal length, depth of field, illumination spot size, beam shape, working distance, polarization, filter wavelength, and attenuation. For example illumination focusing optics 2270 may include one or more actuators for varying these settings according to the configuration parameters that are provided.

Control and processing unit 1400 may additionally or alternatively be interfaced with auxiliary imaging modality assembly 2275. For example, auxiliary imaging modality assembly 2275 may include one or more optical ports, and a mechanism, such as an optical deflection device (e.g. a mirror, prism, reflector, filter, pellicle, window, or optical pick-off) that may be selectively actuated to deflect the beam path along the port axis, thereby directing the optical beam to imaging and/or source optics associated with another imaging modality. For example, in one example implementation, auxiliary imaging modality assembly 2275 may include one or more ports for selectively employing an additional imaging modality including, but not limited to, fluorescence imaging, infrared imaging, ultraviolet imaging, hyperspectral imaging, optical coherence tomography, polarization-sensitive optical coherence tomography, polarization-sensitive imaging, thermal imaging, photo-acoustic imaging, and Raman imaging. Control and processing unit 1400 may thus provide one or more configuration parameters for selectively configuring the imaging system to employ one or more additional or alternative imaging modalities. Control and processing unit 1400 may also provide one or more configuration parameters for selectively configuring the one or more additional or alternative imaging modalities.

In some embodiments, one or more external imaging devices may be employed for multi-modal imaging. For example, multi-modal imaging may be achieved by way of either direct optical imaging, or using the system to hold additional imaging probes, such as MRI, US, PET or X-ray (either in transmit or receive modes). In some embodiments, the turret of robotic arm 102 can be actuated during the procedure to engage different modalities, as described above, much in the way multiple tools are selected in a CNC machining system. In other embodiments, multiple modalities other than optical, for instance ultrasound, MRI, OCT, PET, CT, can be supported by or otherwise interfaced with the automated arm, optionally in addition to one or more optical imaging/detection modalities. In the case of photo-acoustic imaging, laser light is used to excite the tissue, while an ultrasound array positioned in the access port is employed to collect the emitted ultrasound signal. In addition, different wavelengths or spectral bands of light may be utilized. For instance, Raman imaging can be used to investigate the chemical composition of tissue at a specific location of interest, i.e. point source imaging. Hyper-spectral imaging can be accomplished by scanning a detector across the region of interest, or collecting a multi-spectral detector images at a selected location. In one example implementation, the hyperspectral image could be overlaid on video images to provide different perspectives of exposed tissue regions. In another example embodiment, laser light delivered by an optical device supported by the automated arm may be employed for the alignment and/or excitation of photo-reactive therapeutics. Any or all of the optical imaging modes employed by a given system embodiment may be accommodated by a fiber-optic delivery and receiving bundle that is attached to the turret of robotic arm 102.

Alternatively, or in addition, various ports or light guides may be used to co-align the light delivery or reception. In an alternate embodiment, optical system 2250 can have different acquisition modes. Some modes are listed as follows but are not limiting to additional modes not listed here. In one mode, images can be acquired by sweeping through the different image acquisition modes to provide multiple serially obtained (e.g. almost simultaneously obtained) images of different types which can be combined into an overlaid representation and displayed to the operator. The multi modal shifting can be achieved, for example, by using a filter wheel on the optical system, allowing the imaging modalities to change as the wheel is turned. It can also be achieved through beam splitting using optical lenses and directing the beams to different imaging devices. Although several different components are shown interfaced with control and processing unit 1400, it is to be understood that control and processing unit 1400 may be interfaced with any component, or any combination of components, and with other components that are not shown. In an alternate embodiment, the optical system 2250, under control of control and processing system 1400, may automatically perform actions such as, but not limited to, autofocus of the optical view and auto adjustment of the illumination system for optimal viewing illumination, optimal tissue differentiation, and optimal modal detection. Optical system 2250 can achieve these automatic functions through analysis of the various images acquired by the system, such as the optical camera image or others by control and processing system 1400. The images can be analyzed for metrics such as white balance, contrast, and saturation. The metrics can then be processed based on the type of view required, for example when illuminating for tissue differentiation the imaging processing method should employ the constraints of the system (geometric, intensity range, etc.) to obtain the illumination intensity and wavelengths which would provide a suitable (e.g. maximal) contrast metric.

Other image analysis that could be done include image sharpness determination and optimization by analyzing specific focal zones. Alternatively, the optical system 2250 could adjust zoom and focus by calculating the working distance between the camera 1422 and the surgical area of interest by using position and orientation of the surgical tool and position and orientation of the optical system provided by the navigation system. In the case of port-based surgery, the port could be tracked and the zoom and focus be set based on the working distance between the camera and bottom of the port. In both of these cases, a lookup table could be created that relates working distance to a set of camera parameters: zoom, focus, aperture, and iris. This relationship could be determined empirically or analytically. The preceding examples illustrate embodiments in which configuration parameters are provided in a number of data structures pertaining to different devices that may be intra-operatively configured based on the identification of one or more medical instruments. It will be understood that the data structures were illustrated separately for heuristic purposes, and that in other implementations, the two or more data structures may be combined. For example, a composite data structure may be formed in which different devices are provided as different columns. For example, configuration parameters may be provided that stipulate the diameter of illumination spot 2290, and the field of view 2280 provided by imaging optics assembly 2260. Additional configuration parameters may be provided to specify a pre-selected working distance between the distal portion of imaging optics assembly 2260 and the surface of skull 2295, and these additional configuration parameters may be employed to move robotic arm 102 to a suitable position for performing the craniotomy while imaging. In such cases, both optical system 2250 and the patient's skull 2295 may be spatially referenced to enable the relative positioning of optical system 2250. Further examples of configuration parameters that may be obtained based on the identification of the medical instruments include configuration parameters that specify a suitable illumination intensity, spectral profile, colour, or wavelength.

While the teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments, the general scope of which is defined in the appended claims.

The invention claimed is:

1. A medical navigation system for tracking a medical device having a tracking marker attachable to the medical device, the medical navigation system comprising:
   a computing device having a processor coupled to: a memory, a tracking system for tracking the medical device, and a display for displaying an image; and
   an automated arm assembly electrically coupled to the computing device and controlled by a signal provided by the computing device, the automated arm assembly including a plurality of multi-joint arms each having a distal end connectable to respective end effectors, at least one end effector supporting an imaging device electrically coupled to the computing device;
   the computing device being configured to:
   track, based on a signal from the tracking system, a position and orientation of the medical device;
   position the automated arm assembly, based on the tracked position and orientation of the medical device, according to one of at least three modes including:
      automatic alignment of the imaging device to a longitudinal axis and a rotation of the medical device where the medical device is an access port;
      automatic alignment of the imaging device to the longitudinal axis only of the medical device where the medical device is an access port; and
      automatic alignment of a field of view of the imaging device to a point on the medical device; and
   display on the display an image provided by an image signal generated by the imaging device;
   wherein the automatic alignment is performed only when the tracked position and orientation of the medical device has been constant for more than a threshold period of time.

2. The medical navigation system of claim 1, wherein the computing device is further configured to track the distal end or end effector of each multi-joint arm, based on respective signals from the tracking system, and wherein each multi-joint arm is controlled independently based on the respective signals.

3. The medical navigation system of claim 1, wherein each end effector supports respective medical tools, wherein the computing device is further configured to track position and orientation of each medical tool, based on respective signals from the tracking system.

4. The medical navigation system of claim 1, wherein the computing device is further configured to control the imaging device to perform autofocus on a site of interest whenever the imaging device is moved.

5. The medical navigation system of claim 1, wherein the automatic alignment is performed only when the tracked position and orientation of the medical device changes more than a threshold amount.

6. The medical navigation system of claim 1, wherein the automatic alignment is performed only when an estimated occlusion of the field of view of the imaging device is greater than an acceptable occlusion amount.

7. The medical navigation system of claim 1, wherein the automatic alignment is performed in response to an input command.

8. The medical navigation system of claim 7, wherein the input command is provided by at least one of a foot pedal, a joystick, a microphone receiving a voice instruction, a transducer detecting a gesture, and a wireless electronic device.

9. The medical navigation system of claim 1, wherein the computer device is configured to position the automated arm assembly by:
   identifying a site of interest in a predetermined coordinate frame, the site of interest being based on the position and an orientation of the medical device;
   obtaining a position and an orientation for the end effector supporting the imaging device, the position and orientation being defined in the predetermined coordinate frame;
   obtaining a desired standoff distance and a desired orientation between the site of interest and the end effector supporting the imaging device;
   determining a new desired position and a new desired orientation for the end effector based on the position and orientation of the site of interest, the desired standoff distance and the desired orientation; and
   moving the end effector to the new position and orientation.

10. A method for use in a medical navigation system having a computing device including a processor coupled to a memory, a tracking system for tracking a medical device, and a display for displaying an image; and an automated arm assembly electrically coupled to the computing device and controlled by a signal provided by the computing device, the automated arm assembly including a plurality of multi-joint arms each having a distal end connectable to respective end effector, at least one end effector supporting an imaging device electrically coupled to the computing device, the method comprising:
   tracking, based on a signal provided to the computing device by the tracking system, a position and orientation of the medical device;
   positioning the automated arm assembly, based on the tracked position and orientation of the medical device, according to one of at least three modes including:
      automatic alignment of the imaging device to a longitudinal axis and a rotation of the medical device where the medical device is an access port;

automatic alignment of the imaging device to the longitudinal axis only of the medical device where the medical device is an access port; and automatic alignment of a field of view of the imaging device to a point on the medical device; and displaying on the display an image provided by an image signal generated by the imaging device;

wherein the automatic alignment is performed only when the tracked position and orientation of the medical device has been constant for more than a threshold period of time.

11. The method of claim 10, further comprising tracking, by the computing device, the distal end or end effector of each multi-joint arm, based on respective signals from the tracking system, and wherein each multi-joint arm is controlled independently based on the respective signals.

12. The method of claim 10, wherein each end effector supports respective medical tools, the method further comprising tracking, by the computing device, position and orientation of each medical tool, based on respective signals from the tracking system.

13. The method of claim 10, further comprising controlling, by the computing device, the imaging device to perform autofocus on a site of interest whenever the imaging device is moved.

14. The method of claim 10, wherein the automatic alignment is performed only when the tracked position and orientation of the medical device changes more than a threshold amount.

15. The method of claim 10, wherein the automatic alignment is performed only when an estimated occlusion of the field of view of the imaging device is greater than an acceptable occlusion amount.

16. The method of claim 10, wherein the automatic alignment is performed in response to an input command.

17. The method of claim 16, wherein the input command is provided by at least one of a foot pedal, a joystick, a microphone receiving a voice instruction, a transducer detecting a gesture, and a wireless electronic device.

18. The method of claim 10, further comprising positioning the automated arm assembly by:

identifying a site of interest in a predetermined coordinate frame, the site of interest being based on the position and an orientation of the medical device;

obtaining a position and an orientation for the end effector supporting the imaging device, the position and orientation being defined in the predetermined coordinate frame;

obtaining a desired standoff distance and a desired orientation between the site of interest and the end effector supporting the imaging device;

determining a new desired position and a new desired orientation for the end effector based on the position and orientation of the site of interest, the desired standoff distance and the desired orientation; and moving the end effector to the new position and orientation.

* * * * *